(12) United States Patent
Yokota et al.

(10) Patent No.: US 7,837,042 B2
(45) Date of Patent: Nov. 23, 2010

(54) POLYSULFONE TYPE SELECTIVELY PERMEABLE HOLLOW FIBER MEMBRANE MODULE AND PROCESS FOR MANUFACTURING THE SAME

(75) Inventors: Hideyuki Yokota, Otsu (JP); Kimihiro Mabuchi, Otsu (JP); Noriko Monden, Otsu (JP); Noriaki Kato, Otsu (JP); Yuuki Hatakeyama, Osaka (JP); Takashi Sunohara, Osaka (JP); Toshiaki Masuda, Osaka (JP)

(73) Assignee: Nipro Corporation, Osaka-shi (JP)

( * ) Notice: Subject to any disclaimer, the term of this patent is extended or adjusted under 35 U.S.C. 154(b) by 433 days.

(21) Appl. No.: 11/573,333

(22) PCT Filed: Aug. 9, 2005

(86) PCT No.: PCT/JP2005/014562

§ 371 (c)(1),
(2), (4) Date: Aug. 29, 2007

(87) PCT Pub. No.: WO2006/016573

PCT Pub. Date: Feb. 16, 2006

(65) Prior Publication Data

US 2008/0044643 A1    Feb. 21, 2008

(30) Foreign Application Priority Data

Aug. 10, 2004   (JP) .............................. 2004-233450

(51) Int. Cl.
B01D 33/21    (2006.01)
B01D 39/00    (2006.01)

(52) U.S. Cl. ............................. 210/500.23; 210/500.27; 210/500.36; 210/500.41; 210/500.42

(58) Field of Classification Search ............ 210/500.23, 210/500.27, 500.36, 500.41, 500.42
See application file for complete search history.

(56) References Cited

U.S. PATENT DOCUMENTS

| 5,340,480 | A | 8/1994 | Kawata et al. |
| 5,436,068 | A | 7/1995 | Kobayashi et al. |
| 6,432,309 | B1 | 8/2002 | Fuke et al. |
| 7,442,302 | B2 | 10/2008 | Mabuchi et al. |
| 2005/0063859 | A1 | 3/2005 | Masuda et al. |
| 2006/0205309 | A1 * | 9/2006 | Mabuchi et al. ............ 442/338 |
| 2007/0114167 | A1 | 5/2007 | Mabuchi et al. |
| 2007/0187320 | A1 | 8/2007 | Mabuchi et al. |
| 2008/0000830 | A1 | 1/2008 | Mabuchi et al. |
| 2008/0067122 | A1 | 3/2008 | Mabuchi et al. |
| 2008/0087599 | A1 | 4/2008 | Mabuchi et al. |
| 2008/0142434 | A1 | 6/2008 | Mabuchi et al. |

FOREIGN PATENT DOCUMENTS

| CA | 1294745 | | 1/1992 |
| JP | 58-114702 | A | 7/1983 |
| JP | 61-232860 | A | 10/1986 |
| JP | 04-300636 | A | 10/1992 |
| JP | 04-338223 | A | 11/1992 |
| JP | 5-54373 | B2 | 8/1993 |
| JP | 6-165926 | A | 6/1994 |
| JP | 6-75667 | B2 | 9/1994 |
| JP | 6-296686 | A | 10/1994 |
| JP | 7-289863 | A | 11/1995 |
| JP | 09-024261 | A | 1/1997 |
| JP | 11-309355 | A | 11/1999 |
| JP | 2000-140589 | A | 5/2000 |
| JP | 2000-157852 | A | 6/2000 |
| JP | 2000-254222 | A | 9/2000 |
| JP | 2001-38170 | A | 2/2001 |
| JP | 3193262 | B2 | 5/2001 |
| JP | 2001-190934 | A | 7/2001 |
| JP | 2001-205057 | A | 7/2001 |
| JP | 2003-245526 | A | 9/2003 |
| JP | 3551971 | B1 | 5/2004 |
| WO | WO 98/58842 | A1 | 12/1998 |
| WO | WO 2005/051460 | A1 | 6/2005 |

* cited by examiner

Primary Examiner—Lynda Salvatore
(74) Attorney, Agent, or Firm—Leydig, Voit & Mayer, Ltd.

(57) ABSTRACT

The invention relates to a hollow fiber membrane module comprising polysulfone type selectively permeable hollow fiber membranes which contain a polysulfone-based resin and a hydrophilic polymer as main components, wherein (A) the content of the hydrophilic polymer in the uppermost layer of the inner surface of the hollow fiber membrane is at least 1.1 times larger than the content of the hydrophilic polymer in the proximate layer of the inner surface of the membrane, and (B) the content of the hydrophilic polymer in the uppermost layer of the outer surface of the hollow fiber membrane is at least 1.1 times larger than the content of the hydrophilic polymer in the uppermost layer of the inner surface of the membrane. The hollow fiber membrane module is exposed to a radioactive ray, on condition that the oxygen concentration of an ambient atmosphere around the hollow fiber membrane is from 0.001 to 0.1%, and that the moisture content of the hollow fiber membrane to the weight thereof is from 0.2 to 7 mass %.

25 Claims, No Drawings

POLYSULFONE TYPE SELECTIVELY PERMEABLE HOLLOW FIBER MEMBRANE MODULE AND PROCESS FOR MANUFACTURING THE SAME

TECHNICAL FIELD

The present invention relates to hollow fiber membrane modules comprising polysulfone type selectively permeable hollow fiber membranes which are reliable in safety and stability of performance and are easily incorporated into a module and which are particularly suitable for use in blood purifiers, and processes for manufacturing the same.

BACKGROUND OF THE INVENTION

In the hemocatharsis for therapy of renal failure, etc., modules such as hemodialyzers, hemofilters and hemodiafilters, which comprise dialysis membranes or ultrafilter membranes as separators, are widely used in order to remove urinal toxic substances and waste products in blood. Dialysis membranes and ultrafilter membranes as separators are made of natural materials such as cellulose or the derivatives thereof (e.g., cellulose diacetate, cellulose triacetate, etc.) or synthetic polymers such as polysulfone, polymethyl methacrylate, polyacrylonitrile, etc. The importance of modules comprising the hollow fiber membranes as separators is very high in the field of dialyzers, in view of the advantages such as the reduction of the amount of extracorporeal circulated blood, high efficiency of removing undesired substances in blood, and high productivity of manufacturing modules.

Highly water permeable polysulfone-based resins have attracted public attentions, because such resins are most suitable for the advanced dialysis technology, among the above-listed membrane materials. However, semipermeable membranes made of a polysulfone-based resin alone are poor in affinity with blood, inducing airlock phenomena, since the polysulfone-based resin is hydrophobic. Therefore, such semipermeable membranes as they are can not be directly used for treating blood.

To solve this problem, there is proposed a method for imparting hydrophilicity to a membrane by blending a polysulfone-based resin with a hydrophilic polymer: for example, a polyhydric alcohol such as polyethylene glycol or the like is added to a polysulfone-based resin (cf. Patent Literature 1 and Patent Literature 2);

or otherwise, polyvinyl pyrrolidone is added to a polysulfone-based resin (cf. Patent Literature 3 and Patent Literature 4).

These methods are effective to solve the above-discussed problem. However, searching of the optimum conditions for the hydrophilicity-imparting technique by blending a hydrophilic polymer is very important, because the concentration of the hydrophilic polymer in the inner surface of a hollow fiber membrane on the blood-contacting side and the concentration of the hydrophilic polymer in the outer surface thereof give significant influence on the capacities of the hollow fiber membrane. For example, the compatibility of a hollow fiber membrane with blood can be reliably obtained by increasing the concentration of a hydrophilic polymer in the inner surface of the membrane, while too high a concentration of the hydrophilic polymer in the inner surface of the membrane increases the amount of the hydrophilic polymer eluted into blood. Undesirably, the accumulation of the eluted hydrophilic polymer over a long period of dialysis therapy induces side effects or complications.

On the other hand, too high a concentration of the hydrophilic polymer in the outer surface of the membrane deteriorates the endotoxin-adsorbing performance and induces a possibility of the infiltration of endotoxin in a dialyzate into the blood side. As a result, side effects such as fever, etc. are induced, or the hydrophilic polymer in the outer surfaces of the hollow fiber membranes permits the sticking of such membranes to one another while the membranes are being dried, which results in a new problem that the incorporation of such membranes into a module becomes difficult.

On the contrary, a lower concentration of the hydrophilic polymer in the outer surface of the hollow fiber membrane is preferable, since the infiltration of endotoxin into the blood side can be suppressed. However, the hydrophilicity of the outer surface of the hollow fiber membrane becomes lower, which causes a problem in that the outer surface of the hollow fiber membrane becomes poor in compatibility with a physiological saline for use in wetting the membrane, when a bundle of dried hollow fiber membranes is wetted and incorporated into a module. As a result, undesirably, the priming of the membranes (purging the membranes of an air when wetting the same) becomes lower in efficiency.

There is disclosed a method for solving these problems (cf. Patent Literature 5): that is, the concentration of a hydrophilic polymer in the dense layer of the inner surface of a hollow fiber membrane is adjusted within a specified range, and the content of the hydrophilic polymer in the dense layer of the inner surface of the membrane is at least 1.1 times larger than the content of the hydrophilic polymer in the outer surface of the membrane. In particular, this method is based on a technical idea to increase the content of the hydrophilic polymer in the dense layer of the inner surface of the membrane to thereby improve the compatibility thereof with blood, and to decrease the content of the hydrophilic polymer in the outer surface of the membrane to thereby suppress the sticking of the hollow fiber membranes which would occur when drying the membranes. This technique solves one of the problems: i.e., the infiltration of endotoxin in a dialyzate into the blood side is inhibited. However, there still remains unsolved the problem that the priming of the membrane tends to lower because of too low a content of the hydrophilic polymer in the outer surface of the membrane. It is therefore needed to solve this problem.

There is disclosed another method of solving the problem of the infiltration of endotoxin in a dialyzate into the blood side (cf. Patent Literature 6). In this method, the contents of hydrophilic polymers in the proximate layer of the inner surface and the outer surface, and the intermediate layer of a hollow fiber membrane having an uniform membrane structure are specified so as to suppress the infiltration of endotoxin into the blood side. However, also, this method can not solve the problem of lower priming of the membrane, like the former method. In addition, there is a further problem in that the larger size pores of the outer surface of the hollow fiber membrane lower the pressure resistance of the membrane. Therefore, such a membrane has a possibility of bursting when used for hemodiafiltration or the like in which the pressure of a fluid is higher than that for the conventional therapies.

There are further disclosed methods for improving the compatibility of membranes with blood and for reducing the amount of hydrophilic polymers eluted into blood, by specifying the contents of the hydrophilic polymers in the inner surfaces of hollow fiber membranes (cf. Patent Literature 7 to Patent Literature 9).

However, any of the above patent literature does not teach the content of the hydrophilic polymer present in the outer surface of the hollow fiber membrane, and thus, any of the inventions of the above publications is not able to improve all the problems attributed to the content of the hydrophilic polymer present in the outer surface of the hollow fiber membrane.

There is disclosed a method of solving the problem of the infiltration of endotoxin into the blood side, out of the above-discussed problems (cf. Patent Literature 10). This method is devised by taking advantage of the properties of endotoxin which has a hydrophobic moiety in the molecule and which is apt to be adsorbed onto a hydrophobic material. Specifically, in this method, the ratio of a hydrophilic polymer to a hydrophobic polymer in the outer surface of a hollow fiber membrane is adjusted to 5 to 25%. Surely, this method is effective to suppress the infiltration of endotoxin into the side of blood. However, it is needed to remove the hydrophilic polymer in the outer surface of the membrane by washing, so as to impart this feature to the membrane. Accordingly, long treating time is required for this washing, which is disadvantageous in cost. For example, in an Example of the invention of the above patent publication, a hollow fiber membrane is washed by showering with hot water of 60° C. for one hour and washed with hot water of 110° C. for one hour.

This method of decreasing the amount of the hydrophilic polymer in the outer surface of the membrane is effective to inhibit the infiltration of endotoxin into the side of blood. However, the hydrophilicity of the outer surface of the membrane becomes lower, which causes the following disadvantage: when a bundle of hollow fiber membranes dried to be incorporated into a module is again wetted, the hollow fiber membranes are poor in compatibility with physiological saline for wetting the membranes. Undesirably, this method may induce poor priming, i.e., insufficient purging the membranes of an air in the membrane-wetting step. For example, there are disclosed methods of improving this problem, in which a hydrophilic compound such as glyceline or the like is blended (cf. Patent Literature 11 and Paten Literature 12). These methods, however, have problems in that the hydrophilic compound behaves as a foreign matter during dialysis and also tends to deteriorate by light or the like, which gives an adverse influence on the storage stability of a module, and also in that the hydrophilic compound hinders an adhesive from bonding for fixing a bundle of hollow fiber membranes in a module when the membranes are incorporated into the module.

There are disclosed methods of avoiding the sticking of hollow fiber membranes, i.e., another problem out of the foregoing problems: in any of these methods, the ratio of pore areas of the outer surface of a membrane is adjusted to 25% or more (cf. Patent Literature 6 and Patent Literature 13). While these methods are surely effective to prevent the sticking of the hollow fiber membranes, the strength of the membranes becomes lower due to the higher ratio of pore areas, which may lead to the leakage of blood or the like.

Further, a method by specifying the ratio of pore areas and the pore area of the outer surface of a membrane is disclosed (cf. Patent Literature 14).

In the meantime, when a module packed with hollow fiber membranes is used as a medical device, sterilization thereof is indispensable. While the sterilization methods such as sterilization using an ethylene oxide gas or a compressed vapor are conventionally employed, recently, sterilization methods by exposure to radioactive rays have come into wide use, because the exposure to radioactive rays are high in sterilization effect and makes it possible to sterilize a subject matter enveloped in a package with ease. However, the sterilization by way of exposure to radioactive rays brings about decomposed substances from hollow fiber membranes and potting materials, and elution of such decomposed substances may induce side effects in clinical use. There is known a membrane filled with water and sterilized by exposure to a γ-ray, which exhibits high water permeability and which is crosslinked to inhibit the elution of a hydrophilic polymer therefrom. However, this membrane is heavy because of the water filling the same, and thus is poor in handling ease.

To solve this problem, there is disclosed a method for sterilization by exposure to a radioactive ray without using water (cf. Patent Literature 15). In this method, a hollow fiber membrane, adjusted in the oxygen concentration to 0.1 to 3.6% and adjusted in the moisture content to at least 4%, is exposed to a radioactive ray. According to this method, a hollow fiber membrane is evaluated as being low in elution and high in safety, when the amount of consumed aqueous potassium permanganate solution is less than a given value. However, the sterilization of a hollow fiber membrane having a relatively high oxygen concentration of 0.1 to 3.6% by way of exposure to a radioactive ray has a possibility of exciting oxygen radicals under the exposure to the radioactive ray, followed by acceleration of the oxidative decomposition of the materials due to the excited oxygen radicals, which particularly may lead to poor storage stability.

Patent Literature 1: JP-A-61-232860
Patent Literature 2: JP-A-58-114702
Patent Literature 3: JP-B-5-54373
Patent Literature 4: JP-B-6-75667
Patent Literature 5: JP-A-6-165926
Patent Literature 6: JP-A-2001-38170
Patent Literature 7: JP-A-6-296686
Patent Literature 8: JP-A-11-309355
Patent Literature 9: JP-A-2000-157852
Patent Literature 10: JP-A-2000-254222
Patent Literature 11: JP-A-2001-190934
Patent Literature 12: U.S. Pat. No. 3,193,262
Patent Literature 13: JP-A-7-289863
Patent Literature 14: JP-A-2000-140589
Patent Literature 15: JP-A-2003-245526

DISCLOSURE OF THE INVENTION

An object of the present invention is to provide a hollow fiber membrane module which is light in weight and is non-frozen because of non-use of a filler liquid, and which comprises polysulfone type selectively permeable hollow fiber membranes which are reliable in safety and performance stability and can be incorporated into a module with ease and which are especially suitable for use in a blood purifier. Other objects of the present invention are to provide a hollow fiber membrane module which is free of a possibility of the elution of the decomposed substances of hollow fiber membranes, a potting material, etc. due to exposure to a radioactive ray, and to provide a process for manufacturing the same.

Means for Solving the Problems

That is, the present invention relates to a hollow fiber membrane module which includes polysulfone type hollow fiber membranes comprising a polysulfone-based resin and a hydrophilic polymer as main components, and this module is characterized in that (A) the content of the hydrophilic polymer in the uppermost layer of the inner surface of the is at least 1.1 times larger than the content of the hydrophilic polymer in the proximate layer of the inner surface of the membrane;

(B) the content of the hydrophilic polymer in the uppermost layer of the other surface of the polysulfone type hollow fiber membrane is at least 1.1 times larger than the content of the hydrophilic polymer in the uppermost layer of the inner surface of the membrane on the blood-contacting side; and (C) the hollow fiber membrane of which the moisture content to its weight is from 0.2 to 7 mass % is exposed to a radioactive ray under an ambient atmosphere having an oxygen concentration of from 0.001 to 0.1%.

The present invention also relates to a process for manufacturing a hollow fiber membrane module, which includes a step of the above radiation exposure.

In one aspect of the present invention, the content of the hydrophilic polymer in the uppermost layer of the inner surface of the membrane is, in general, preferably 5 to 60 mass %, more preferably 10 to 50 mass %, still more preferably 20 to 40 mass %. The content of the hydrophilic polymer in the proximate layer adjacent to the uppermost layer is generally about 2 to about 37 mass %, optimally about 5 to about 20 mass %. Further, the content of the hydrophilic polymer in the outer surface of the hollow fiber membrane is about 25 to about 50 mass % which is enough to control the content of the hydrophilic polymer in the uppermost layer of the outer surface of the membrane to be at least 1.1 times larger than the content of the hydrophilic polymer in the uppermost layer of the inner surface of the membrane. The contents of the hydrophilic polymer in the respective layers as above are selected so that the amount of the hydrophilic polymer eluted from the hollow fiber membrane can be 10 ppm or less.

EFFECT OF THE INVENTION

The hollow fiber membrane module of the present invention is highly reliable in safety and stability of its performance, and has a high water permeability suitable for therapy of chronic renal failure. The hollow fiber membrane module of the present invention can be used in a dry state, and thus is light in weight and has no possibility of freezing. Therefore, the hollow fiber membrane module of the present invention is handled with ease and is suitably used for a high performance blood purifier. Further, the hollow fiber membrane module of the present invention has safety as a medical device, since infiltration of eluted substances as foreign matters to a human body can be inhibited.

BEST MODES FOR CARRYING OUT THE INVENTION

Hereinafter, the present invention will be explained in more detail.

The hollow fiber membrane to be used in the present invention comprises a polysulfone-based resin containing a hydrophilic polymer. The polysulfone-based resin referred to in the present invention is the generic term of resins having sulfone bonds. Preferable examples of the polysulfone-based resin include, but not limited to, polysulfone resins and polyethersulfone resins both of which have repeating units represented by the formula [I] or [II] and which are commercially available with ease.

[Chemical formula 1]

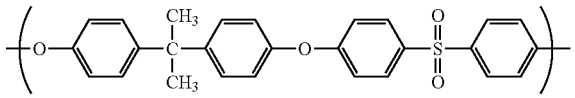

[Chemical formula 2]

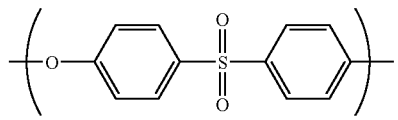

Examples of the hydrophilic polymer referred to in the present invention include materials such as polyethylene glycol, polyvinyl alcohol, polyvinyl pyrrolidone, carboxylmethyl cellulose, polypropylene glycol, glycerin, starches, and derivatives thereof. Preferably, polyvinyl pyrrolidone having a weight average molecular weight of 10,000 to 1,500,000 is used in view of safety and cost-effectiveness. In concrete, preferably used are polyvinyl pyrrolidone having a molecular weight of 9,000 (K17), polyvinyl pyrrolidone having a molecular weight of 45,000 (K30), polyvinyl pyrrolidone having a molecular weight of 450,000 (K60), polyvinyl pyrrolidone having a molecular weight of 900,000 (K80) and polyvinyl pyrrolidone having a molecular weight of 1,200,000 (K90) which are commercially available form BASF. Each of the above hydrophilic polymers may be used alone or in combination with one or more of the above polymers having different molecular weights, or in combination with one or more of different resins, according to an intended use, or in order to obtain intended properties or structure.

In the present invention, (A) the content of the hydrophilic polymer in the uppermost layer of the inner surface of the hollow fiber membrane is at least 1.1 times larger than the content of the hydrophilic polymer in the proximate layer of the inner surface of the membrane, as mentioned above. Preferably, the content of the hydrophilic polymer in the proximate layer, adjacent to the uppermost layer, of the inner surface of the membrane is about 2 to about 37 mass %, in order to control the content of the hydrophilic polymer in the uppermost layer to be larger than the content of the hydrophilic polymer in the proximate layer and to optimally control the content of the hydrophilic polymer in the uppermost layer to 20 to 40 mass %. Practically, the proper content of the hydrophilic polymer in the proximate layer of the surface of the membrane is about 5 to about 20 mass % because of this reason. In detail, the multiplying factor for the difference in content is allowed up to maximum 10 or so. When the multiplying factor exceeds this limit, the diffusion and transfer of the hydrophilic polymer may reversely proceed from the uppermost layer to the proximate layer in the surface of the membrane, and the manufacturing of a hollow fiber membrane having a structure allowing such a multiplying factor is difficult. A proper content of the hydrophilic polymer in the uppermost layer of the inner surface of the membrane can be calculated simply by multiplying the value (5 to 20 mass %) of the proper content of the hydrophilic polymer in the proximate layer in the surface of the membrane, by the value of a multiplying factor of about 1.1 to about 10. By doing so, the optimum value of 20 to 40 mass % is obtained. Preferably, the hydrophilic polymer is contained in the uppermost layer in such an amount that is usually about 1.1 to about 5 times larger, and as the case may be, optimally about 1.2 to about 3 times larger than the content of the hydrophilic polymer in the proximate layer. Practically, the multiplying factor can be optionally selected in consideration of the capacity of the hollow fiber membrane. For example, when the content of the hydrophilic polymer in the proximate layer of the surface of the membrane is 5 mass % as the lower limit, the content of the hydrophilic polymer in the uppermost layer in the surface of the membrane is appropriately 20 to 40 mass % which is equivalent to a value 4 to 8 times larger than the content of the hydrophilic polymer in the above proximate layer.

In the present invention, (B) the content of the hydrophilic polymer in the uppermost layer of the outer surface of the polysulfone type hollow fiber membrane is at least 1.1 times larger than the content of the hydrophilic polymer in the uppermost layer of the inner surface of the membrane, as mentioned above. In this regard, the content of the hydrophilic polymer in the uppermost layer of the outer surface of the hollow fiber membrane is preferably about 25 to about 50 mass %. When the content of the hydrophilic polymer in this layer is too small, the amount of protein in blood adsorbed to the support layer of the hollow fiber membrane tends to increase, and undesirably, the compatibility of the membrane with blood and the permeability of the membrane tend to lower. On the contrary, when the content of the hydrophilic polymer in the uppermost of the outer surface of the membrane is too large, there may be a high possibility of the infiltration of endotoxin in a dialyzate into the blood side, which may induce side effects such as fever, etc. in a patient, or which may cause a disadvantage that the membranes are hard to be incorporated into a module because of the sticking of such hollow fiber membranes due to the hydrophilic polymer in the surfaces of the membranes, when the membranes are dried.

In the present invention, the content of the hydrophilic polymer in the polysulfone-based resin is not particularly limited, and it may be optionally selected, in so far as sufficient hydrophilicity and high wettability can be imparted to the hollow fiber membrane. The ratio of the hydrophilic polymer is preferably 1 to 20 mass %, more preferably 3 to 15 mass %, relative to 80 to 99 mass % of the polysulfone-based resin. When the ratio of the hydrophilic polymer is too low, the hydrophilicity-imparting effect may be poor. On the other hand, when the ratio of the hydrophilic polymer is too high, the hydrophilicity-imparting effect saturates, and the amount of the hydrophilic polymer eluted from the membrane increases and may exceed 10 ppm, as will be described later.

As mentioned above, one of the features of the present invention rests in that (C) the oxygen concentration of the ambient atmosphere around the hollow fiber membrane is 0.001 to 0.1%, and in that the hollow fiber membrane of which the moisture content to its weight is adjusted to 0.2 to 7 mass % is exposed to a radioactive ray. Preferably, the radiation exposure is conducted on a hollow fiber membrane module enveloped in a package. However, the hollow fiber membrane module may be exposed to a radioactive ray, and then may be enveloped in a package.

The radiation exposure is equivalent to the sterilization which is an indispensable process for the manufacturing of medical devices, and also is equivalent to the insolubilization of the hydrophilic polymer by way of crosslinking, as one of the preferred modes of the present invention. When radiation exposure is carried out under an atmosphere containing oxygen, oxygen radicals tend to form and increase the sterilization effect. However, the oxygen radicals attack the polymer material and may acceleratedly oxidize and decompose the polymer material. When the oxygen concentration of the ambient atmosphere is less than 0.001%, the sterilization effect becomes poor. When this concentration exceeds 0.1%, the oxidation and decomposition of the polymer material tend to proceed. When the moisture content of the hollow fiber membrane is less than 0.2 mass %, it becomes hard to crosslink the hydrophilic polymer, and the amount of the eluted substances increases. When the moisture content of the membrane exceeds 7 mass %, the weight of the hollow fiber membrane module increases; the hollow fiber membrane module becomes wet, which permits the proliferation of bacteria; or the potting agent reacts with water to foam the potting agent or to increase the amount of eluted substances.

The foregoing preferred modes of the present invention will be described in more detail based on the technical features. That is, in the preferred modes of the present invention, a polysulfone type selectively permeable hollow fiber membrane which contains a hydrophilic polymer and which simultaneously satisfies the following features can be obtained:

(1) the amount of the hydrophilic polymer eluted from the hollow fiber membrane is 10 ppm or less;
(2) the content of the hydrophilic polymer in the uppermost layer of the inner surface of the polysulfone type hollow fiber membrane is 20 to 40 mass %;
(3) the content of the hydrophilic polymer in the proximate layer of the inner surface of the polysulfone type hollow fiber membrane is 5 to 20 mass %; and
(4) the content of the hydrophilic polymer in the uppermost layer of the outer surface of the polysulfone type hollow fiber membrane is 25 to 50 mass %, and is at least 1.1 times larger than the content of the hydrophilic polymer in the uppermost layer of the inner surface of the membrane.

In the present invention, the amount of the hydrophilic polymer eluted from the hollow fiber membrane is preferably 10 ppm or less (feature 1). When this amount exceeds 10 ppm, there is a possibility of inducing side effects or complications due to the eluted hydrophilic polymer over a long period of dialysis therapy. To obtain this feature, for example, the amounts of the hydrophilic polymer to the hydrophobic polymer in the respective layers are controlled within the foregoing ranges, or otherwise, the conditions for manufacturing the hollow fiber membrane are optimized.

In the present invention, as mentioned above, the content of the hydrophilic polymer in the uppermost layer of the inner surface of the polysulfone type hollow fiber membrane is preferably 20 to 40 mass % (feature 2). The content of the hydrophilic polymer in the uppermost layer of the inner surface of the polysulfone type hollow fiber membrane can be optionally selected within a wide range of 5 to 60 mass %, for example, 10 to 50 mass %. In order to advantageously attain the effect of the present invention, preferably, the uppermost layer of the inner surface of the hollow fiber membrane comprises 60 to 80 mass % of the polysulfone-based resin and 20 to 40 mass % of the hydrophilic polymer as main components. When the content of the hydrophilic polymer is less than 20 mass %, the hydrophilicity of the surface of the hollow fiber membrane on the blood-contacting side becomes lower, which leads to poor compatibility of the membrane with blood, resulting in a likely blood coagulation on the surface of the hollow fiber membrane. The coagulated thrombus clogs the hollow fiber membrane and consequently degrades the separating capacity of the hollow fiber membrane or increases the amount of the blood left to remain therein after subjected to hemodialysis. The content of the hydrophilic polymer in the uppermost layer of the inner surface of the hollow fiber membrane is preferably 21 mass % or more, more preferably 22 mass % or more, still more preferably 23 mass % or more. On the other hand, when this content exceeds 40 mass %, the amount of the hydrophilic polymer eluted into the blood increases, and such an eluted hydrophilic polymer has a possibility of inducing side effects or complication over a long period of hemodialysis therapy. Therefore, the content of the hydrophilic polymer in the uppermost layer of the inner surface of the hollow fiber membrane is preferably 39 mass % or less, more preferably 38 mass % or less, still more preferably 37 mass % or less.

In the present invention, as mentioned above, the content of the hydrophilic polymer in the proximate layer of the inner surface of the polysulfone type hollow fiber membrane is preferably 5 to 20 mass % (feature 3). The proximate layer of the inner surface of the polysulfone type hollow fiber membrane comprises 60 to 99 mass % of the polysulfone-based resin and 1 to 40 mass % of the hydrophilic polymer, as main components, which may be optionally selected within the above ranges, respectively. The content of the hydrophilic polymer is preferably 5 to 20 mass %, and in general, more preferably 7 to 18 mass %. The content of the hydrophilic polymer in the uppermost layer in the inner surface of the polysulfone type hollow fiber membrane is preferably larger in view of compatibility with blood, as mentioned above. However, there is an antinomy in that the increase of the content of the hydrophilic polymer leads to the increase of the amount of the hydrophilic polymer eluted into the blood. Therefore, the content of the hydrophilic polymer is about 20 to about 40 mass %, which is selected in consideration of the appropriate range thereof.

The content of the hydrophilic polymer in the proximate layer of the inner surface of the hollow fiber membrane may be selected within a relatively wide range of 1 to 40 mass %. However, there is a disadvantage when the content of the hydrophilic polymer in the proximate layer is larger than the content of the hydrophilic polymer in the uppermost layer (for example, when the content of the hydrophilic polymer in the uppermost layer is 30 mass %, and that in the proximate layer, 35 mass %): that is, the diffusion and transfer of the hydrophilic polymer from the proximate layer to the uppermost layer of the inner surface of the membrane is accelerated, with the result that, undesirably, the content of the hydrophilic polymer in the uppermost layer becomes larger than the predetermined value. To sum up, in consideration of a mechanism in which the hydrophilic polymer is transferred to the uppermost layer by the amount of the hydrophilic polymer consumed in the uppermost layer, through the diffusion and transfer of the hydrophilic polymer, the content of the hydrophilic polymer in the proximate layer of the surface of the membrane is relatively smaller than that in the uppermost layer, and is preferably, for example, 19 mass % or less, more preferably 18 mass % or less. When the content of the hydrophilic polymer in the proximate layer of the inner surface of the hollow fiber membrane is too small, it is impossible to transfer the hydrophilic polymer from the proximate layer to the uppermost layer, which may lower the stability of the solute-removing capacity or the blood compatibility of the hollow fiber membrane. The optimum content of the hydrophilic polymer in the proximate layer of the inner surface of the hollow fiber membrane is, therefore, more preferably 6 mass % or more, still more preferably 7 mass % or more. In general, the content of the hydrophilic polymer in the proximate layer of the surface of the hollow fiber membrane is slightly larger than the content of the hydrophilic polymer in the main components, that is, 80 to 99 mass % of the polysulfone-based polymer and 1 to 20 mass % of the hydrophilic polymer, which constitute the hollow fiber membrane of the present invention.

This feature 3 is one of the factors which make it possible to overcome the foregoing antinomy and to optimize this event at a higher level than any of the conventional techniques has done. In other words, the content of the hydrophilic polymer in the uppermost layer of the hollow fiber membrane, which dominantly affects the blood compatibility of the membrane, is set at the lowest level which is enough to allow the exhibition of the blood compatibility. However, there arises another problem in that, although this content of the hydrophilic polymer in the uppermost layer can permit the exhibition of the initial blood compatibility, the hydrophilic polymer in the uppermost layer is eluted into blood bit by bit over a long period of hemodialysis, which gradually lowers the blood compatibility over a long period of hemodialysis. The persistency of the blood compatibility of the polysulfone type hollow fiber membrane is improved by specifying the content of the hydrophilic polymer in the proximate layer of the inner surface of the hollow fiber membrane. By specifying the content of the hydrophilic polymer in the proximate layer of the surface of the hollow fiber membrane, the above problem can be solved, which is the decrease of the content of the hydrophilic polymer in the uppermost layer due to the elution of the hydrophilic polymer of the uppermost layer into blood in association with the proceeding of hemodialysis, and the aged deterioration of the blood compatibility of the membrane attributed to the above decrease of the content of the hydrophilic polymer (or the decrease in the persistency of blood compatibility). This method is accomplished based on the technical idea that the transfer of the hydrophilic polymer in the proximate layer of the surface of the hollow fiber membrane, to the uppermost layer thereof can compensate for the decrease of the content of the hydrophilic polymer in the uppermost layer. Accordingly, less than 5 mass % of the content of the hydrophilic polymer in the proximate layer of the inner surface of the hollow fiber membrane may be possibly insufficient to suppress the deterioration of the consistency of the blood compatibility of the hollow fiber membrane. On the other hand, when the content of the hydrophilic polymer in the proximate layer of the surface of the hollow fiber membrane on the blood-contacting side exceeds 20 mass %, the amount of the hydrophilic polymer eluted into blood tends to increase, which may possibly induce side effects or complications over a long period of hemodialysis therapy. Hitherto, the proximate layer of the surface of the hollow fiber membrane, a proper content of the hydrophilic polymer in the proximate layer and the dispersing condition of the hydrophilic polymer attributed to its structure have not been clarified, and the present inventors have firstly clarified these matters based on their novel findings.

In the present invention, as mentioned above, the content of the hydrophilic polymer in the uppermost layer of the outer surface of the polysulfone type hollow fiber membrane is 25 to 50 mass %, and is preferably at least 1.1 times larger than the content of the hydrophilic polymer in the uppermost layer of the inner surface of the membrane (feature 4). Too small a content of the hydrophilic polymer in the outer surface of the hollow fiber membrane may possibly lower the blood compatibility and permeability of the hollow fiber membrane, since the amount of protein in blood, adsorbed onto the support layer of the hollow fiber membrane, tends to increase. The outer surface of the hollow fiber membrane may comprise 90 to 40 mass % of the polysulfone-based resin and 10 to 60 mass % of the hydrophilic polymer as the main components. Practically, the content of the hydrophilic polymer in the outer surface of the hollow fiber membrane is more preferably 27 mass % or more, still more preferably 29 mass % or more. In case of dried hollow fiber membranes, the priming capacity of the membranes may become poor. Too large a content of the hydrophilic polymer in the outer surface of the membrane, on the contrary, may induce higher possibility of infiltration of endotoxin in the dialyzate into the blood side. As a result, side effects such as fever, etc. may be induced; or the hollow fiber membranes tend to stick to one another because of the hydrophilic polymer present on the surfaces of the membranes when the membranes are dried, and this may make it hard to incorporate such membranes into a module. The content of the hydrophilic polymer in the outer surface of the hollow fiber membrane is more preferably 43 mass % or less, still more preferably 40 mass % or less.

As one aspect of the feature 4, the content of the hydrophilic polymer in the uppermost layer of the outer surface of the hollow fiber membrane is preferably at least 1.1 times larger than the content of the hydrophilic polymer in the uppermost layer of the inner surface thereof. The content of the hydrophilic polymer gives some influence on the shrinkage percentage of the hollow fiber membrane. With the increase of the content of the hydrophilic polymer, the shrinkage percentage of the resultant hollow fiber membrane tends to increase. For example, when the content of the hydrophilic polymer in the uppermost layer of the inner surface of the membrane is larger than the content of the hydrophilic polymer in the uppermost layer of the outer surface of the membrane, the difference in shrinkage percentage between the inner surface and the outer surface of the membrane may cause microwrinkles on the inner surface of the hollow fiber membrane or break the hollow fiber membrane. The wrinkles formed on the inner surface of the hollow fiber membrane facilitates the accumulation of the protein in blood on the surface of the membrane, when the blood is allowed to pass through the hollow fiber membranes for hemodialysis. This may induce a problem that the permeability of the membrane degrades with time. For this reason, it is preferable to design so that the content of the hydrophilic polymer in the outer surface of the hollow fiber membrane can be larger than that in the inner surface thereof.

The hollow fiber membrane of the present invention further has a dense layer in the inner surface, and has a structure in which the sizes of pores are gradually increased toward the outer surface of the membrane. Since the void ratio of the outer surface of the membrane is higher than that of the inner surface thereof, the shrinkage percentage of the outer surface of the membrane becomes larger. In consideration of this influence, the content of the hydrophilic polymer in the uppermost layer of the outer surface of the membrane is preferably at least 1.1 times, more preferably at least 1.2 times, still more preferably at least 1.3 times larger than the content in the uppermost layer of the inner surface of the membrane.

For the reasons as described above, the better, the larger the content of the hydrophilic polymer in the uppermost layer of the outer surface of the hollow fiber membrane. However, there may be some problems, when the content of the hydrophilic polymer in the uppermost layer of the outer surface of the hollow fiber membrane is 2.0 or more times larger than that in the uppermost layer of the inner surface thereof: that is, the content of the hydrophilic polymer relative to the content of the polysulfone-based polymer becomes too large, which may lead to the insufficient strength of the hollow fiber membrane, the sticking of the hollow fiber membranes to one another, the back flow of endotoxin during hemodialysis and the elution of the hydrophilic polymer. The content of the hydrophilic polymer in the uppermost layer of the outer surface of the hollow fiber membrane is more preferably at most 1.9 times, still more preferably at most 1.8 times, far more preferably at most 1.7 times larger than that in the uppermost layer of the inner surface thereof.

In another aspect, preferably, the hydrophilic polymer is crosslinked so as to be insoluble. There is no limit in selection of the crosslinking method or the degree of crosslinking. For example, crosslinking by exposure to γ-ray, electron ray or heat, or chemical crosslinking is carried out. Above all, crosslinking by exposure to γ-ray or electron ray is preferable in the following points: any residue such as an initiator or the like does not remain; the degree of penetration into the materials is high; and sterilization of the membrane can be made concurrently with the crosslinking.

The insolubilization, herein referred to, has connection with the solubility of the crosslinked hollow fiber membrane in dimethylformamide. The insolubilization of the crosslinked membrane is evaluated as follows: 1.0 g of the crosslinked membrane is cut out and then is dissolved in 100 mL of dimethylformamide, and the insoluble portion of the membrane is visually observed for evaluation. In case of a module filled with a liquid, firstly, the liquid is removed; then, pure water is allowed to pass through the passage on the side of a dialyzate at a rate of 500 mL/min. for 5 minutes; then, similarly, pure water is allowed to pass through the passage on the side of blood at a rate of 200 mL/min. for 5 minutes; and finally, pure water is allowed to pass from the side of blood to the side of the dialyzate as if permeating the membrane, at a rate of 200 mL/min., so as to wash the membrane. The hollow fiber membrane is removed from the module and is freeze-dried. This freeze-dried membrane is used as a sample for measuring the insoluble component. Also, in case of a dried hollow fiber membrane module, the similar washing is done to prepare a sample for measurement.

The inner surface of the hollow fiber membrane has a two-layer structure attributed to the difference in concentration of the hydrophilic polymer between the uppermost layer and the proximate layer. In the hollow fiber membrane, the sizes of pores tend to increase from the dense layer of the inner surface of the membrane toward the outer surface thereof, and therefore, the inner surface of the membrane is likely to have a two-layer structure attributed to the difference in density between the uppermost layer and the proximate layer. The thickness of the respective layers and their interface is optionally changed according to the conditions for manufacturing the hollow fiber membrane. In addition, the structures of the layers give some influence on the performance of the hollow fiber membrane. While it can be recognized that there are seemingly formed two layers in the inner surface of the membrane, their definite interface can not be recognized, in consideration of the situation where the uppermost layer and the proximate layer are almost concurrently formed adjacent to each other, in the light of the manufacturing step of the hollow fiber membrane by way of the coagulation thereof. When the distribution curve of the content of the hydrophilic polymer in the interface portion between the two layers is investigated, the distribution curve appears as a continuous line in many cases. From this fact, it can be supposed that there may be difference in concentration between the two layers, which is attributed to the difference in the content of the hydrophilic polymer. In general, a fault occurs in the distribution curve of the content of the hydrophilic polymer in the interface between the two layers. Therefore, there are technical difficulties in the assumption of the formation of two discontinuous layers whose materials differ in behavior from each other. It is optimal to control the content of the hydrophilic polymer in the uppermost layer to 20 to 40 mass % and the content of the hydrophilic polymer in the proximate layer to 5 to 20 mass %. However, the designing for controlling the content of the hydrophilic polymer in the uppermost layer to, for example, 40 mass % and the content of the hydrophilic polymer in the proximate layer to, for example, 5 mass % may make it impossible for the resultant membrane to sufficiently function, in consideration of the mechanism in which the hydrophilic polymer diffuses and transfers from the proximate layer to the uppermost layer of the surface of the membrane. In other words, it is also important to design the membrane by paying attentions on the simple difference in the content of the hydrophilic polymer between the two layers. For example, the difference (the multiplying factor of at least 1.1) in the content (mass %) of the hydrophilic polymer between the uppermost layer and the proximate layer is converted into the difference in the mass % of the contents of the hydrophilic polymer between the two layers. Then, the simple difference in content of the hydrophilic polymer between the respective layers is controlled to, preferably about 1 to about 35 mass %, optimally about 5 to about 25 mass %. Under this condition, the diffusion and transfer of the hydrophilic polymer from the proximate layer to the uppermost layer of the surface of the membrane can proceed smoothly. For example, when the content of the hydrophilic polymer in the uppermost layer is 32 mass %, the content of the hydrophilic polymer in the proximate layer is 7 to 27 mass %, which satisfies the above preferable condition, i.e., the multiplying factor of about 1.1 to about 10.

In this regard, the content of the hydrophilic polymer in the uppermost layer of the hollow fiber membrane is measured and calculated by the ESCA method as will be described later, and the absolute value of the content in the uppermost layer (having a depth of several to several tens angstrom from the surface) of the hollow fiber membrane is determined. In general, it is possible to measure the content of the hydrophilic polymer (e.g., polyvinyl pyrrolidone (PVP)) in a layer which has a depth of up to about 10 nm (100 angstrom) from the surface of the hollow fiber membrane by the ESCA method (uppermost layer ESCA).

In the meantime, the content of the hydrophilic polymer in the proximate layer of the surface of the hollow fiber membrane is found by the evaluation of the absolute value of the ratio of the hydrophilic polymer in a layer which has a depth equivalent to several hundreds nm from the surface. According to the ATR method (the proximate layer ATR), it is possible to measure the content of the hydrophilic polymer in a layer which has a depth of about 1,000 to about 500 nm (1 to 1.5 μm) from the surface of the hollow fiber membrane.

The contents of the hydrophilic polymer in the inner surface and the outer surface of the hollow fiber membrane have some connection with the molecular weight of the hydrophilic polymer. For example, polyvinyl pyrrolidone having a low molecular weight (about 450,000) shows higher solubility and is largely eluted in the coagulation, and largely diffuses and transfers, as compared with polyvinyl pyrrolidone having a high molecular weight (about 1,200,000). For this reason, there is formed a hollow fiber membrane which has relatively high concentrations of the hydrophilic polymer in the respective layers, that is, 20 to 40 mass % of the hydrophilic polymer in the uppermost layer and 5 to 20 mass % of the hydrophilic polymer in the proximate layer in the surface of the membrane, in comparison with an average content (1 to 20 mass %) of the hydrophilic polymer relative to the polysulfone-based polymer. A hollow fiber membrane may be formed using polyvinyl pyrrolidones having different molecular weights in combination. For example, when a hollow fiber membrane is manufactured from 80 mass % of a polysulfone-based resin, and 15 mass % of a polyvinyl pyrrolidone having a molecular weight of 900,000 and 5 mass % of a polyvinyl pyrrolidone having a molecular weight of about 45,000, this membrane designing may give some influences on the contents of the polyvinyl pyrrolidones in the two layers and the performance of the hollow fiber membrane. Designing of a hollow fiber membrane made from this point of view is also included in the scope of the present invention.

To attain the foregoing features 2, 3 and 4 of the present invention, for example, the mass ratio of the hydrophilic polymer to the hydrophobic polymer is controlled within the above specified range, and the conditions for manufacturing the hollow fiber membrane are optimally controlled. In concrete, preferably, a dense layer formed on the side of the inner surface of the hollow fiber membrane has a two-layer structure which has difference in density between the uppermost layer and the proximate layer. When the mass ratio of the hydrophilic polymer to the polysulfone-based polymer in a spinning dope, and the concentration and temperature of an interior-coagulating solution are controlled within ranges as will be explained later, the coagulating rates and/or the phase-separating rates of the uppermost layer and the proximate layer of the inner surface of the hollow fiber membrane become different from each other, and also, the polysulfone-based polymer and the hydrophilic polymer become different from each other in the solubility in a solvent/water. It is considered that, for these differences, the features 2 and 3 can be exhibited, although the particular reasons therefor have not been known.

Regarding the feature 4, the important point is to optimize the conditions for drying the hollow fiber membrane: when a wet hollow fiber membrane is dried, the hydrophilic polymer dissolved in water tends to transfer from the inner portion of the hollow fiber membrane to the surface thereof, accompanying the transfer of the water. By employing drying conditions as will be described later in this stage, it becomes possible to cause a certain difference in the transfer of water and also to even up the water-transferring rate in a whole of the hollow fiber membrane, so that the hydrophilic polymer in the hollow fiber membrane can immediately transfer to both the surfaces of the membrane without forming any spot. Since the evaporation of water from the outer surface of the membrane is larger in amount than that from the inner surface thereof, the amount of the hydrophilic polymer transferring to the outer surface of the membrane is larger accordingly, and thus, it is supposed that the feature 4 of the hollow fiber membrane of the present invention can be attained.

The mass ratio of the hydrophilic polymer (e.g. PVP) to the polysulfone-based polymer in the spinning dope is preferably 0.1 to 0.6. When the content of PVP in the dope is too small, it is likely to become difficult to control the ratios of the hydrophilic polymer in the respective layer of the membrane within the ranges specified by the features 2, 3 and 4. Therefore, the ratio of the hydrophilic polymer to the polysulfone-based polymer in the dope is preferably at least 0.15, more preferably at least 0.2, still more preferably at least 0.25, and particularly at least 0.3. When the content of the hydrophilic polymer in the dope is too large, the content of the hydrophilic polymer in the membrane also becomes larger, which requires hard washing of the membrane, resulting in higher cost. Therefore, the ratio of the hydrophilic polymer in the dope is more preferably 0.57 or less, still more preferably 0.55 or less.

The interior-coagulating solution is preferably an aqueous solution of 15 to 70 mass % of dimethylacetamide (DMAc). When the concentration of the interior-coagulating solution is too low, the coagulating rate of the inner surface of the membrane becomes higher, which sometimes makes it hard to control the content of the hydrophilic polymer in the proximate layer of the inner surface of the membrane. Therefore, the concentration of the interior-coagulating solution is more preferably 20 mass % or more, still more preferably 25 mass % or more, far more preferably 30 mass % or more. When the concentration of the interior-coagulating solution is too high, the coagulating rate of the inner surface of the membrane becomes lower, which makes it hard to control the content of the hydrophilic polymer in the uppermost layer of the inner surface of the membrane. Therefore, the concentration of the interior-coagulating solution is more preferably 60 mass % or less, still more preferably 55 mass % or less, far more preferably 50 mass % or less. Further, it is preferable to control the temperature of the interior-coagulating solution within a range of −20 to 30° C. When the temperature of the interior-coagulating solution is too low, the uppermost layer of the surface of the membrane coagulates immediately after the extrusion of the dope through a nozzle, which makes it hard to control the content of the hydrophilic polymer in the proximate layer of the inner surface of the membrane. Therefore, the temperature of the interior-coagulating solution is more preferably −10° C. or higher, still more preferably 0° C. or higher, particularly 10° C. or higher. When the temperature of the interior-coagulating solution is too high, there occurs too large a difference in the membrane structure (condensation and rarefaction) between the uppermost layer and the proximate layer of the inner surface of the membrane, which makes it hard to control the contents of the hydrophilic polymer in the uppermost layer and the proximate layer of the inner surface of the membrane. Therefore, the temperature of the interior-coagulating solution is more preferably 25° C. or lower, still more preferably 20° C. or lower. By controlling the temperature of the interior-coagulating solution within the above specified range, it becomes possible to inhibit the bubbling of the gases dissolved in the interior-coagulating solution, when the interior-coagulating solution is extruded through the nozzle. By inhibiting the bubbling of the gasses dissolved in the interior-coagulating solution, the following secondary effects are produced: that is, the breaking of the membrane fiber just under the nozzle and the formation of knobs on the membrane fiber can be suppressed. To control the temperature of the interior-coagulating solution within the above specified range, it is preferable to provide a heat exchanger in the piping from an interior-coagulating solution tank to the nozzle.

In one of specific preferred methods of drying wet hollow fiber membranes, a bundle of wet hollow fiber membranes is put in a microwave drier and is dried by exposure to microwave with an output of 0.1 to 20 kW under a reduced pressure of 20 kPa or lower. The higher an output of microwave, the better, in view of the reduction of drying time. However, it is preferable not to excessively increase the output of microwave, since the hydrophilic polymer in the hollow fiber membrane, if excessively dried or heated, is deteriorated or decomposed, or the membrane tends to lower in wettability in use. Therefore, the output of microwave is more preferably 18 kW or lower, still more preferably 16 kW or lower, particularly 14 kW or lower. While even lower than 0.1 kW of output of microwave is possible to dry a bundle of hollow fiber membranes, longer drying time is required, which may lead to less treating amount. The output of microwave is therefore more preferably 0.15 kW or higher, still more preferably 0.2 kW or higher. The reduced pressure which is employed in combination with the output of microwave is more preferably 15 kPa or lower, still more preferably 10 kPa or lower, which may vary depending on the moisture content of the bundle of the hollow fiber membranes, found before the drying step. The lower the reduced pressure, the better, since the drying speed can be increased. However, the lower limit of the reduced pressure is preferably 0.1 kPa or higher, more preferably 0.2 kPa or higher, still more preferably 0.3 kPa or higher, in consideration of an increased cost for improving the sealing degree of the system. Preferably, the optimum values of the output of microwave and the reduced pressure are determined by experiments, because such optimum values change depending on the moisture content of the bundle of hollow fiber membranes and the number of hollow fiber membranes in the bundle.

The referential drying conditions of the present invention are described: for example, when a bundle of 20 hollow fiber membranes, each of which has a moisture content of 50 g, is dried, the total moisture content is 1,000 g (50 g×20=1,000 g), and the output of microwave suitable for this total moisture content is 1.5 kW, and the reduced pressure suitable therefor is 5 kPa.

The frequency of the microwave is preferably 1,000 to 5,000 MHz, more preferably 1,500 to 4,500 MHz, still more preferably 2,000 to 4,000 MHz, so as to inhibit the formation of exposure spots on the bundle of hollow fiber membranes, and in view of the effect of pushing water out of the pores of the membranes.

It is important to uniformly heat and dry the bundle of hollow fiber membranes while the membranes being dried by exposure to microwave. In this microwave drying, reflected waves incidental to the generation of microwaves cause non-uniform heating, and therefore, it is important to employ a means for reducing the non-uniform heating which is caused by the reflected waves. Such a means is not limited and may be optionally selected: for example, a reflecting plate is provided in an oven to reflect the reflected waves thereon to thereby uniform the heating, as disclosed in JP-A-2000-340356.

Preferably, the hollow fiber membranes are dried within 5 hours under the application of microwaves in combination with the reduced pressure. When the drying time is too long, the transfer speed of water in the hollow fiber membrane is low, which may give some influence on the transfer of the hydrophilic polymer dissolved in the water. As a result, it becomes impossible to transfer the hydrophilic polymer to the intended site (or layer) in the hollow fiber membrane, or spots attributed to such transfer tend to occur, so that it becomes impossible to control the contents of the hydrophilic polymer in the respective sites (or layers). Therefore, the hollow fiber membrane-drying time is more preferably within 4 hours, still more preferably within 3 hours. The shorter the drying time, the better it is for the manufacturing efficiency. However, the drying time is preferably 5 minutes or longer, more preferably 10 minutes or longer, still more preferably 15 minutes or longer, when the frequency and output of microwave are so selected in combination with the reduced pressure as to prevent the deterioration or decomposition of the hydrophilic polymer due to the heating and as to inhibit the formation of spots during the drying step.

Further, the highest temperature of the hollow fiber membrane while being dried is preferably 80° C. or lower. When this temperature is too high, there is a possibility of the hydrophilic polymer's deterioration and decompostion. Therefore, the temperature of the hollow fiber membrane being dried is more preferably 75° C. or lower, still more preferably 70° C. or lower. On the contrary, when this temperature is too low, the drying time becomes longer, which may make it hard to control the amounts of the hydrophilic polymer in the respective sites of the hollow fiber membrane, as described above. Therefore, the temperature of the hollow fiber membrane being dried is preferably 2° C. or higher, more preferably 30° C. or higher, still more preferably 40° C. or higher.

Further, it is preferable not to bone-dry the hollow fiber membrane. If bone-dried, the wettability of the hollow fiber membrane tends to lower when the membrane is again wetted for use, or the hydrophilic polymer becomes hard to absorb water and thus may be easily eluted from the hollow fiber membrane. Therefore, the moisture content of the dried hollow fiber membrane is preferably 1 mass % or more, more preferably 1.5 mass % or more. When the moisture content of the hollow fiber membrane is too high, the propagation of bacteria may be facilitated during the storage of the hollow fiber membrane, or the hollow fiber membrane may be crushed by its own weight. Therefore, the moisture content of the hollow fiber membrane is preferably 5 mass % or less, more preferably 4 mass % or less, still more preferably 3 mass % or less. In this regard, the moisture content (mass %) referred to in the present invention can be readily calculated by the following equation:

$$\text{Moisture content (mass \%)}=100\times(a-b)/b$$

wherein a represents the mass of the hollow fiber membrane before drying, and b represents the mass of the hollow fiber membrane after the drying.

In the present invention, the ratio of pore areas of the outer surface of the hollow fiber membrane is 8 to 25%, and the average pore area of the void portion of the outer surface of the hollow fiber membrane is 0.3 to 1.0 $\mu m^2$. These specific conditions are effective to impart the above features to the hollow fiber membrane, and thus are preferred modes. When the ratio of pore areas is less than 8% and when the average pore area is less than 0.3 $\mu m^2$, the coefficient of water permeability of the membrane tends to lower. Further, such hollow fiber membranes tend to stick to one another due to the hydrophilic polymer present on the outer surfaces of the membranes while the membranes are being dried, and thus are hard to be incorporated into a module. Therefore, the ratio of pore areas is more preferably 9% or more, still more preferably 10% or more. The average pore area is more preferably 0.4 $\mu m^2$ or more, still more preferably 0.5 $\mu m^2$ or more, far more preferably 0.6 $\mu m^2$ or more. On the contrary, when the ratio of pore areas exceeds 25% and when the average pore area exceeds 1.0 $\mu m^2$, the burst pressure of the membrane tends to lower. Therefore, the ratio of pore areas is more preferably 23% or less, still more preferably 20% or less, far more preferably 17% or less, and particularly 15% or less. The average pore area is more preferably 0.95 $\mu m^2$ or less, still more preferably 0.90 $\mu m^2$ or less.

In order to control the content of the hydrophilic polymer and the ratio of pore areas of the outer surface of the hollow fiber membrane within the above specified ranges, the optimization of the conditions for washing the manufactured hollow fiber membranes is also effective, in addition to the adjustment of the content of the hydrophilic polymer to the polysulfone-based polymer in the spinning dope and the optimization of the conditions for drying the hollow fiber membranes. As the membrane-manufacturing conditions, it is effective to optimize the temperature and humidity of the air gap of the outlet of a nozzle, the dope-drawing condition and the temperature and the composition of an exterior-coagulation bath. As the washing method, washing with hot water or alcohol and centrifugal washing are effective.

Preferably, the air gap is enclosed with a material capable of shielding the air gap from an external air. Preferably, the humidity of the air gap is controlled according to the composition of the spinning dope, the temperature of the nozzle, the length of the air gap, and the temperature and composition of the exterior-coagulation bath. For example, a spinning dope (polyethersulufone/polyvinyl pyrrolidone/dimethylacetamide/water=10 to 25/0.5 to 12.5/52.5 to 89.5/0 to 10.0) is extruded from a nozzle of 30 to 60° C., and is then allowed to pass through an air gap with a length of 100 to 1,000 mm and is guided to an exterior-coagulation bath having a concentration of 0 to 70 mass % and a temperature of 50 to 80° C. In this case, the absolute humidity of the air gap is 0.01 to 0.3 kg/kg in a dry air. By controlling the humidity of the air gap within this range, it becomes possible to control the ratio of pore areas, the average pore area and the content of the hydrophilic polymer of the outer surface of the hollow fiber membrane within the proper ranges, respectively.

The exterior-coagulating solution is preferably an aqueous solution of 0 to 50 mass % of DMAc. When the concentration of the exterior-coagulating solution is too high, the ratio of pore areas and the average pore area of the outer surface of the hollow fiber membrane become too large, which is likely to induce a possibility of accelerating the backflow of endotoxin to the side of blood during hemodialysis. Therefore, the concentration of the exterior-coagulating solution is more preferably 40 mass % or less, still more preferably 30 mass % or less, far more preferably 25 mass % or less. On the contrary, when the concentration of the exterior-coagulating solution is too low, a large amount of water is needed to dilute the solvent which is brought from the spinning dope, and the cost for disposal of waste liquid increases. Therefore, the lower limit of the concentration of the exterior-coagulating solution is more preferably 5 mass % or more.

In the manufacturing of the hollow fiber membrane of the present invention, it is preferable not to substantially draw the semi-solid hollow fiber membrane before the structure of the hollow fiber membrane has been fixed. The wording of "not to substantially draw the semi-solid hollow fiber membrane" means that the velocities of rollers used in the spinning step are so controlled as not to loose or excessively pull a filament-like spinning dope extruded from a nozzle. The ratio of the linear speed of the extrusion to the velocity of the first roller in the coagulation bath (draft ratio) is preferably 0.7 to 1.8. When this ratio is less than 0.7, the hollow fiber membrane being fed may be loosen, which leads to poor productivity. When this ratio exceeds 1.8, the structure of the membrane is likely to be destructed: for example, the dense layer of the hollow fiber membrane is spilt. The draft ratio is more preferably 0.85 to 1.7, still more preferably 0.9 to 1.6, and particularly 1.0 to 1.5. When the draft ratio is adjusted within this range, the deformation or destruction of the pores of the membrane can be prevented, and the clogging of the pores of the membrane with the protein in blood can be prevented. Thus adjusted, the hollow fiber membrane can exhibit stable performance with time, and also can exhibit sharp fractional properties.

The hollow fiber membrane having passed through a water bath is directly wound in a wet state onto a hank, so as to make up a bundle of 3,000 to 20,000 hollow fiber membranes. Then, the resulting bundle of hollow fiber membranes is washed to remove the excessive solvent and hydrophilic polymer. In the present invention, preferably, the bundle of hollow fiber membranes is immersed in hot water of 70 to 130° C., or an aqueous solution of 10 to 40 vol. % of ethanol or isopropanol of a room temperature to 50° C. for washing.

(1) In the washing with hot water, the bundle of hollow fiber membranes is immersed in excessive RO water and treated at a temperature of 70 to 90° C. for 15 to 60 minutes, and then is removed from the bath and subjected to centrifugal dehydration. This operation is repeated 3 or 4 times while RO water is being replaced.

(2) The bundle of hollow fiber membranes immersed in excessive RO water is treated at 121° C. in a compressed container for about 2 hours.

(3) In the washing with an aqueous solution of ethanol or isopropanol, preferably, the same operation as the above operation (1) is repeated.
(4) The bundle of hollow fiber membranes is radially laid in a centrifugal washing machine and is subjected to centrifugal washing for 30 minutes to 5 hours, while washing water of 40 to 90° C. is being shower-like blown thereonto from the center of the rotation.

Each of the above washing methods may be carried out in combination with one or more of the above methods. When the treating temperature is too low in any of the above methods, it is needed to increase the number of washing times, which leads to higher cost. On the contrary, when the treating temperature is too high, the decomposition of the hydrophilic polymer is accelerated, and thus, the washing efficiency, on the contrary, becomes poor. By washing the bundle of hollow fiber membranes as above, the content of the hydrophilic polymer in the outer surface of the membrane is properly adjusted, which makes it possible to inhibit the sticking of the membranes and to decrease the amount of eluted substances.

In the present invention, it is important to concurrently attain the foregoing features 1 to 4 to thereby make it possible to satisfy all the foregoing properties.

In the present invention, it is important to treat a hollow fiber membrane module which comprises the hollow fiber membrane concurrently satisfying the foregoing features 1 to 4, as follows:
(5) the oxygen concentration of an atmosphere in the hollow fiber membrane module and/or around the hollow fiber membrane is controlled to from 0.001 to 0.1%, and under this atmosphere, the hollow fiber membrane of which the moisture content to its weight is controlled to 0.2 to 7 mass % is exposed to a radioactive ray.

As has been already described, this radiation exposure is equivalent to a sterilization treatment indispensable for the manufacturing of medical devices, and is also to insolubilize the hydrophilic polymer by crosslinking the same, as one of preferred modes of the present invention. When the radiation exposure is carried out in the presence of oxygen, there form oxygen radicals, which enhance the sterilization effect, however, which are likely to attack the polymer materials to oxidize and decompose the same. When the oxygen concentration of the ambient atmosphere is lower than 0.001%, the sterilization effect becomes poor. When this oxygen concentration is higher than 0.1%, the oxidation and decomposition of the polymers are accelerated. In the meantime, when the moisture content of the hollow fiber membrane is less than 0.2 mass %, the crosslinking of the hydrophilic polymer becomes hard, and the amount of eluted hydrophilic polymer tends to increase. When the moisture content thereof is larger than 7 mass %, the mass of the hollow fiber membrane module becomes larger, and the module in such a wet state permits the proliferation of bacteria, and the reaction of the potting agent with water causes the foaming of the potting agent and increases the amount of eluted substances. In the present invention, it is possible for the hollow fiber membrane to attain the various properties by the foregoing methods. However, it is not until the hollow fiber membrane maintains these preferable properties in practical use that the same membrane can exhibit its effect in a clinical site. It is indispensable to sterilize the hollow fiber membrane by radiation exposure under the above conditions, which are one of the features of the present invention, in order that the sterilized hollow fiber membrane can exhibit its properties which the same hollow fiber membrane possessed before the sterilization. The radioactive ray to be employed is an electro ray, γ-ray, neutron ray, X-ray or the like, among which γ-ray is preferable in view of the effects of maintaining the properties of the membrane and sterilizing the membrane.

If the sterilization by way of radiation exposure is carried in an atmospheric air, excited oxygen radicals break the main chains of the polymers and decompose them. Under such a situation, the radiation exposure of the hollow fiber membrane module is preferably carried out under an atmosphere of an inert gas in the hollow fiber membrane module and/or around the hollow fiber membrane. However, it is difficult to perfectly displace the atmosphere in the hollow fiber membrane module with an inert gas. In the present invention, the hollow fiber membrane module is air-tightly enveloped in a gas-impermeable packaging medium, together with an oxygen scavenger, and is then left to stand for a given time to thereby remove the oxygen in the packaging medium. This method makes it possible to selectively remove the oxygen from the air in the packaging medium because of the presence of the oxygen scavenger, and thus, the inner atmosphere of the hollow fiber membrane module is of an inert nitrogen gas. The inert gas to be used in the present invention means a gas poor in reactivity, such as carbon dioxide, nitrogen, argon, helium or the like. In general, an oxygen scavenger is put in a packaging bag and is sealed therein, and the packaging bag is left to stand for about 48 hours to thereby decrease the oxygen concentration in the packaging bag to 0.1% or lower, although this result changes depending on the type of an oxygen scavenger and the dimensions of a packaging bag. Accordingly, preferably, the hollow fiber membrane module sealed in the packaging bag is exposed to a radioactive ray after at least 2 days has been passed since the sealing of the hollow fiber membrane module. If this period of time up to the radiation exposure after the sealing is too long, bacteria tend to proliferate. Therefore, the radiation exposure is carried out within preferably 10 days, more preferably 7 days, still more preferably 5 days, after the sealing of the hollow fiber membrane module, together with the oxygen scavenger.

When the radiation dose is too large, the materials of the membrane tend to disintegrate. When the radiation dose is too small, the sterilization effect is insufficient. The radiation dose is preferably 10 to 50 kGy, more preferably 10 to 30 kGy, in case of using γ-ray as a radioactive ray. When the radiation dose of γ-ray is less than the lower limit, the sterilization effect tends to lower. When the radiation dose of γ-ray is more than the upper limit, the decomposition of the materials tends to accelerate.

The radiation exposure under the above conditions may be carried out by employing any of the following methods:
(6) the hollow fiber membrane module is sealed in a packaging bag together with an oxygen scavenger, and is then exposed to a radioactive ray while the inner atmosphere of the packaging bag is regulated to 25° C. and higher than 40% RH, or
(7) the hollow fiber membrane module is sealed in a packaging bag together with an oxygen scavenger capable of releasing the moisture content, and is then exposed to a radioactive ray.

A higher relative humidity is preferable, since the stabilization of the hydrophilic polymer due to the partial crosslinking thereof is accelerated by the radiation exposure. The relative humidity is preferably at least 45% RH, more preferably 50% RH, still more preferably 55% RH. However, too high a relative humidity permits dewing on the surface of the hollow fiber membrane and within the packaging bag, which may degrade the quality of the resultant product. Therefore, the relative humidity is preferably at most 95% RH, more preferably at most 90% RH, still more preferably 85% RH. In this regard, the relative humidity referred to in the present invention can be calculated by the following equation:

Relative humidity (% RH)=100×p/P wherein p represents a water vapor partial pressure at a room temperature, and P represents a saturated water vapor pressure at a room temperature.

In the present invention, the above effect can be exhibited by controlling the relative humidity of the inner atmosphere of the packaging bag, with the proviso that the relative humidity around the hollow fiber membrane in the hollow fiber membrane module is maintained within the above range. Therefore, preferably, the inner atmosphere of the hollow fiber membrane module which includes therein the hollow fiber membranes is communicated with an exterior within the packaging bag.

In the present invention, the method for controlling the relative humidity in the inner atmosphere of the packaging bag to higher than 40% RH is not limited. However, preferably employed is the method described in the paragraph (7), that is, the method for exposing, to a radioactive ray, the hollow fiber membrane module sealed in the packaging bag together with the oxygen scavenger capable of releasing the moisture content. The packaging bag herein preferably used has an oxygen permeability of at most 1 cm$^3$/(m$^2$0.24 h.atm) (20° C., 90% RH) and/or a water vapor permeability of at most 5 g/(m$^2$0.24 h.atm) (40° C., 90% RH). Preferable examples of a material for the packaging bag are oxygen- and water vapor-impermeable materials such as an aluminum film, aluminum-deposited film, inorganic oxide-deposited film of silica and/or alumina, vinylidene chloride polymer composite film and the like. The packaging bag may be sealed by any of the heat sealing method, impulse heat sealing method, fusion sealing method, frame sealing method, ultrasonic sealing method, high frequency sealing method and the like. Thus, the material for the packaging bag is preferably a composite material of a film having a sealing property and any of the above impermeable materials. Particularly preferable is a laminate sheet comprising a structural layer of an aluminum foil capable of efficiently shutting out an oxygen gas and a water vapor, an outer layer of a polyester film, an intermediate layer of an aluminum foil, and an inner layer of a polyethylene film, since this laminate sheet has both of impermeability and a heat sealing property.

Examples of the oxygen scavenger include sulfite, hydrogensulfite, dithionite, hydroquinone, catechol, resorcinol, pyrogallol, gallic acid, rongalite, ascorbic acid and/or a salt thereof, sorbose, glucose, lignin, dibutylhydroxytoluene, dibutylhydroxyanisole, ferrous salt, metal powder (e.g. iron powder, etc.) and the like. The oxygen scavenger is appropriately selected from these materials for use. An oxygen scavenger mainly comprising metal powder, if needed, may contain, as an oxidation catalyst, one or more compounds selected from halogenated metal compounds such as sodium chloride, potassium chloride, magnesium chloride, calcium chloride, aluminum chloride, ferrous chloride, ferric chloride, sodium bromide, potassium bromide, magnesium bromide, calcium bromide, iron bromide, nickel bromide, sodium iodide, potassium iodide, magnesium iodide, calcium iodide, iron iodide, etc. As a method for imparting a moisture-releasing function, a moisture-release type oxygen scavenger (e.g. Ageless® Z-200PT manufactured by Mitsubishi Gas Chemical Company, Inc.) or a porous carrier such as zeolite powder impregnated with moisture is included in a packaging bag together with the hollow fiber membrane module. Additionally, other functional fillers such as a deodorant may be included in the packaging bag. The form of the oxygen scavenger is not limited, and it may be in the form of powder, particles, mass or sheet; or it may be a sheet- or film-shaped oxygen scavenger obtained by dispersing an oxygen absorber composition in a thermoplastic resin.

In the hollow fiber membrane module subjected to radiation exposure under the above conditions, the formation of various extracted substances attributed to the deterioration of the hollow fiber membrane included in the module is inhibited, and the amount of eluted hydrogen peroxide and/or the amount of consumed aqueous solution of potassium permanganate ($2.0 \times 10^{-3}$ mol/L) are decreased to predetermined amount(s) or less, which are the preferred modes of the present invention to be exhibited. Thus, the reliability in safety of the hollow fiber membrane module is markedly improved when in use for hemocatharsis.

The hollow fiber membrane module of the present invention exhibits the following features after having undergone the above radiation exposure:
(8) the amount of hydrogen peroxide eluted from the hollow fiber membrane which is removed from the hollow fiber membrane module after 3 months has passed since the radiation exposure is 10 ppm or less, and/or
(9) The amount of a consumed aqueous solution of potassium permanganate ($2.0 \times 10^{-3}$ mol/L) used of the titration of the eluted substance in 10 mL of the initial washing liquid is 5 mL or less per 1 m$^2$ of the inner surface of the hollow fiber membrane.

According to the approved standards for manufacturing dialyzer type artificial kidney devices, it is regulated that a maximum UV absorbance measured at 220 to 350 nm in an elution test should not exceed 0.1. However, recently, it has been known that the formation of components which can not be detected by the UV absorptionmetry is likely to give some influence on the safety of the hollow fiber membrane. One of such components is hydrogen peroxide which is supposed to be formed by radiation exposure or other treatment in the presence of oxygen. Hydrogen peroxide induces the deterioration of the materials for the hollow fiber membrane and increases the UV absorbance with the passage of time after the radiation exposure, and hydrogen peroxide itself concurrently increases in amount with the passage of time, which is likely to accelerate the deterioration of the materials of the membrane and to further increase the amount of the eluted substance. In the present invention, the amount of hydrogen peroxide extracted from the hollow fiber membrane after 3 or more months has passed since the radiation exposure is preferably 10 ppm or less, more preferably 8 ppm or less, still more preferably 6 ppm or less. When the amount of eluted hydrogen peroxide is too large, the deterioration of the hollow fiber membrane is induced, and thus, the use of such a deteriorated hollow fiber membrane for blood treatment brings about a high possibility of releasing an eluted substance into blood, which is likely to induce side effects or complications when the hollow fiber membrane is used over a long period of time.

An index for attaining higher safety from other point of view is the amount of consumed potassium permangnoate. The elution test using a circuit according to the approved standards for manufacturing dialysis type artificial kidney devices is conducted by way of titration of 10 mL of an elute with an aqueous solution of potassium permangnoate ($2.0 \times 10^{-3}$ mol/L). This standard regulates that the amount of potassium permanganate consumed for the titration should be 1 mL or less. This standard is for a test of an eluted substance from a circuit, and is more strict than the approved standard for a dialyzer. Therefore, a hollow fiber membrane module is not needed to clear this standard, but is preferable to clear the same standard to attain higher safety. The initial washing liquid referred to in the present invention is 10 mL sampled from 25 mL of a washing liquid which flows out in first 15 seconds after the hollow fiber membrane module has been filled with a physiological salt solution which was allowed to pass through the hollow fiber membrane module at a flow rate of 100 mL/minute for the measurement of a substance eluted from the hollow fiber membrane module. To measure the eluted substance contained in the initial washing liquid, 20 mL of an aqueous solution of potassium permanganate ($2.0 \times 10^{-3}$ mol/L) and 1 mL of diluted hydrochloric acid are added, and the mixture is boiled for 3 minutes, and is then cooled to a room temperature. Then, 1 mL of an aqueous solution of potassium iodide is added, and the mixture is sufficiently stirred and left to stand for 10 minutes. The resultant solution is then subjected to titration using an aqueous solution of sodium thiosulfate ($1.0 \times 10^{-2}$ mol/L). The difference between the amount of the aqueous solution of sodium thiosulfate consumed for the titration of a physiological salt solution which has not been passed through the hollow fiber membrane module and the amount of the aqueous solution of sodium thiosulfate consumed for the titration of the initial washing liquid is defined as the amount of the aqueous solution of potassium permanganate consumed by the eluted substance (i.e. the amount of the consumed aqueous solution of potassium permanganate).

To obtain such a small amount of eluted substance, it is preferable to carry out the foregoing radiation exposure. In the present invention, the use of PVP having a hydrogen peroxide content of 300 ppm or less is preferable for the manufacturing of the hollow fiber membrane. By controlling the hydrogen peroxide content in PVP as a starting material to 300 ppm or less, the amount of hydrogen peroxide eluted from the resultant hollow fiber membrane bundle can be decreased to 5 ppm or less, and thus, the quality of the hollow fiber membrane bundle of the present invention can be stabilized. Accordingly, the hydrogen peroxide content in polyvinyl pyrrolidone as the starting material is more preferably 250 ppm or less, still more preferably 200 ppm or less, particularly 150 ppm or less.

Hydrogen peroxide contained in PVP used as the staring material is supposed to form in the course of the oxidization and deterioration of PVP. Therefore, it is effective to take a measure to suppress the oxidation deterioration of PVP in the course of preparing PVP, in order to decrease the hydrogen peroxide content in PVP to 300 ppm or less. It is also effective to take a measure to suppress the deterioration of PVP in the course of the transportation or storage of PVP. For example, preferably, PVP is enveloped in an aluminum foil laminate bag to be shielded from light, and concurrently, an inert gas such as a nitrogen gas or the like is charged in such a bag, together with an oxygen scavenger, for the storage of the PVP. On the other hand, when the same bag is opened to divide the PVP into small portions for use, such a divided portion of PVP is weighed or charged under an ambient atmosphere replaced with an inert gas, or such a divided portion of PVP is stored under the same conditions as taken above. In the meantime, the inner atmosphere of a supply tank or the like in a raw material-supplying system is preferably replaced with an inert gas, in the course of manufacturing the hollow fiber membrane. It is also acceptable to decrease the amount of hydrogen peroxide by the recrystallization method or the extraction method.

The hollow fiber membrane module of the present invention comprises hollow fiber membranes having a burst pressure of 0.5 MPa or higher, and preferably has a coefficient of water permeability of 150 mL/m$^2$/hr/mmHg or more.

The burst pressure herein referred to is an index of the pressure resistant capacity of hollow fiber membranes in the form of a module. The burst pressure is measured as follows: the interior space of the hollow fiber membrane is compressed with an air while the compression pressure is being gradually increased, and a pressure which bursts the hollow fiber membrane when the membrane can not withstand the internal pressure thereof is measured. The higher the burst pressure, the less the latent defects of the hollow fiber membrane which will cause cutting and pin pores in the hollow fiber membrane in use. Therefore, the burst pressure is preferably 0.5 MPa or higher, more preferably 0.7 MPa or higher and particularly 1.0 MPa or higher. When the burst pressure is lower than 0.5 MPa, it may be impossible to detect such latent defects of the hollow fiber membrane that leads to the leakage of blood as will be described later. While a higher and higher burst pressure is preferred, it becomes impossible to obtain a desired membrane performance, if the thickness of the membrane is increased or the void ratio is excessively decreased in order to increase the burst pressure. Therefore, the burst pressure is preferably lower than 2.0 MPa, more preferably lower than 1.7 MPa, still more preferably lower than 1.5 MPa and particularly lower than 1.3 MPa, when the hollow fiber membranes are intended to be used as a hemodialyzer.

In the meantime, when the coefficient of water permeability is less than 150 mL/m$^2$/hr/mmHg, the solute permeability tends to lower. When the size or the number of the pores of the membrane is increased in order to improve the solute permeability, the strength of the membrane tends to lower or defects are caused in the membrane. In this regard, the hollow fiber membrane of the present invention is decreased in resistance to solute-permeation and improved in membrane strength in good balance by optimizing the pore size of the outer surface of the membrane, thereby optimizing the void ratio of the support layer portion in the outer surface of the membrane. The coefficient of water permeability is more preferably 200 mL/m$^2$/mmHg or more, still more preferably 300 mL/m$^2$/mmHg or more, far more preferably 400 mL/m$^2$/mmHg or more, and particularly 500 mL/m$^2$/mmHg or more. On the other hand, when the coefficient of water permeability is too high, the water-removing control during a hemodialysis therapy becomes hard. Therefore, the coefficient of water permeability is preferably 2,000 mL/m$^2$/mmHg or less, more preferably 1,800 mL/m$^2$/mmHg or less, still more preferably 1,500 mL/m$^2$/mmHg or less, far more preferably 1,300 mL/m$^2$/mmHg or less, and particularly 1,000 mL/m$^2$/mmHg or less.

In the final stage for providing a commercial product, a module for use in blood purification is usually subjected to a leak test in which the interior or the exterior of a hollow fiber membrane is compressed with an air in order to check any defect of the hollow fiber or the module. When a leak is detected by the compressed air, such a module is scraped as a defective or such a defect is repaired. The air pressure for use in the leak test is, in many cases, several times larger than the proof pressure of hemodialyzers (generally 500 mmHg). However, in case of very highly water permeable hollow fiber membranes for use in blood purification, microflaws, crushing or tearing thereof which can not be detected by any of the conventional compression leak tests would cause the cutting or pin pores of the hollow fiber membranes, in the course of the manufacturing steps after the leak test (mainly in the step of sterilization or packing), in the course of transportation, or in the course of handling in a clinical site (unpacking or priming); and such cutting or pin pores of the membranes are likely to cause troubles such as the leakage of blood during a therapy. These troubles can be avoided by specifying the burst pressure as above.

Adjusting the non-uniformity in thickness of hollow fiber membranes is also effective to suppress the occurrence of the foregoing latent defects. The non-uniformity in thickness means the non-uniformity of the thickness of 100 hollow fiber membranes in a module, found when the sections of the hollow fiber membranes are observed. The non-uniformity in thickness is preferably indicated by a ratio of a minimum value of the thickness to a maximum value thereof. Preferably, the non-uniformity per 100 hollow fiber membranes is 0.6 or more. When even only one hollow fiber membrane having a non-uniformity of smaller than 0.6 is included in 100 hollow fiber membranes, such a hollow fiber membrane may cause a latent defect which will lead to the leakage of blood during a clinical therapy. Therefore, the non-uniformity referred to in the present invention is not an average value of non-uniformity of the 100 hollow fiber membranes but a minimum value thereof. The higher the non-uniformity, the better, because the uniformity of the membranes is improved to thereby suppress the development of latent defects of the membranes and to increase the burst pressure. Therefore, the non-uniformity in membrane thickness is more preferably 0.65 or more, still more preferably 0.7 or more, far more preferably 0.75 or more. When the non-uniformity is smaller than 0.6, the latent defects of the membranes tend to occur as actual defects, and the burst pressure becomes lower, which is likely to induce the leakage of blood.

To improve the non-uniformity in the thickness of the membrane to 0.6 or more, for example, it is preferable to strictly uniform the width of the slit of a nozzle, namely, the outlet for extruding a membrane-forming solution. Generally used as a spinning nozzle for hollow fiber membranes is a tube-in-orifice type nozzle which has an annular portion for extruding a spinning dope and has a hole for extruding a core solution as a hollow portion-forming solution, inside the annular portion. The width of the slit indicates the width of the outer annular portion for extruding the spinning dope. By lessening the variation in the width of the slit, the non-uniformity of the thickness of spun hollow fiber membranes can be decreased. Specifically, the ratio of a maximum value to a minimum value of the width of the slit is 1.00 to 1.11, and preferably, the difference between the maximum value and the minimum value is preferably 10 μm or less, more preferably 5 μm or less. Also effective are the optimization of the temperature of the nozzle, the decrease of extrusion spots of the interior core solution formed in the course of manufacturing membranes, the optimization of the multiplying factor for drawing, etc.

To further increase the burst pressure, the flaws of the surface of the hollow fiber membrane and the foreign matters and bubbles included in the membrane are decreased to thereby decrease the latent defects of the membrane. To prevent the occurrence of flaws on the surface of the membrane, it is effective to optimize the conditions of the materials for rollers and guides used in the steps of manufacturing hollow fiber membranes, and the roughness of the surfaces of the materials. It is also effective to decrease the number of times of contact between a module casing and the hollow fiber membranes or the number of frictions between each of the hollow fiber membranes, when the bundle of the hollow fiber membranes is inserted into the module casing to make up a module. In the present invention, the rollers to be used is preferably planished at their surfaces in order to prevent the hollow fiber membranes from slipping and having flaws at their surfaces. The surfaces of the guides to be used are preferably matte-finished or knurly finished to reduce the resistance attributed to the contact with the hollow fiber membranes as much as possible. The bundle of hollow fiber membranes is not directly inserted into the module casing, but preferably, the bundle of hollow fiber membranes wrapped in a matte-finished film is inserted in the module casing, and then, only the film is removed from the module casing.

To prevent the hollow fiber membranes from including foreign matters, it is effective to use materials containing less foreign matters, or to decrease the amount of foreign matters by filtering the spinning dope. In the present invention, the spinning dope is filtered through a filter having pores with diameters smaller than the thickness of the hollow fiber membrane. Specifically, the spinning dope which is homogeneously dissolved is allowed to pass through a sintered filter which has pores with diameters of 10 to 50 μm and which is located between a dissolution tank and a nozzle. The filtering may be done at least once, however, it is preferable to carry out the filtering treatment in a plurality of steps in order to improve the filtering efficiency and to prolong the life of the filter. The diameter of the pores of the filter is more preferably 10 to 45 μm, still more preferably 10 to 40 μm. When the diameter of the pores of the filter is too small, the back pressure increases, and the quantitative evaluation of the extrusion of the spinning dope tends to degrade.

To prevent the inclusion of bubbles in the membranes, it is effective to degas the spinning solution. Stationary degassing or decompression degassing may be employed in accordance with the viscosity of the spinning dope. In concrete, the inner space of a dissolution tank is decompressed to −100 to −750 mmHg, and then is sealed, and the tank is left to stand in a still state for 5 to 30 minutes. This operation is repeated several times for degassing the tank. When the decompression degree is too low, it is needed to increase the number of times of degassing, which requires longer time. When the decompression degree is too high, higher cost is needed to improve the sealing degree of the system. The total time for the degassing treatment is preferably 5 minutes to 5 hours. When the treating time is too long, the hydrophilic polymer may be deteriorated or decomposed because of the decompression effect. When the treating time is too short, the effect of degassing becomes insufficient.

EXAMPLES

Hereinafter, the effect of the present invention will be explained by way of Examples thereof, which should not be construed as limiting the scope of the present invention in any way. The methods of evaluating the physical properties of the following Examples are described below.

1. Coefficient of Water Permeability

The circuit on the side of the blood outlet of a module (on the side of the outlet from a pressure-measuring point) was blocked with a forceps. A compression tank was charged with pure water maintained at 37° C., and pure water was fed to the interior of the hollow fiber membrane insulated in a constant-temperature bath of 37° C. while the pressure was being controlled with a regulator, and the amount of a filtrate flowing to the outside of the hollow fiber membrane was measured with a graduated cylinder. The transmembrane pressure difference (TMP) is expressed by the equation:

$$TMP = (Pi + Po)/2$$

[in the equation, Pi represents the pressure on the side of the inlet of the module; and Po, the pressure on the side of the outlet thereof]. The TMP was changed at four points, and the flow amount of the filtrate was measured, and the coefficient of water permeability (mL/hr./mmHg) was calculated from the slope indicting the relationship between TMP and the flow amount of the filtrate. In this regard, the coefficient of correlation between TMP and the flow amount of the filtrate must be 0.999 or more. To reduce an error in pressure loss due to the circuit, TMP was measured within a range of 100 mmHg or lower. The coefficient of water permeability of the hollow fiber membrane was calculated from the area of the membrane and the coefficient of water permeability of the module:

$$UFR(H) = UFR(D)/A$$

[in the equation, UFR(H) represents the coefficient of water permeability (mL/m$^2$/hr/mmHg) of the hollow fiber membrane; UFR(D) represents the coefficient of water permeability (mL/hr/mmHg) of the module; and A represents the area (m$^2$) of the membranes in the module].

2. Calculation of the Area of Membranes

The area of membranes in a module was calculated by the following equation, based on the inner diameter of the hollow fiber membrane:

$$A = n \times \pi \times d \times L$$

[in the equation, n represents the number of hollow fiber membranes in the module; π represents the ratio of the circumference of a circle to its diameter; d represents the inner diameter (m) of the hollow fiber membrane; and L represents the effective length (m) of the hollow fiber membranes in the module].

3. Burst Pressure

The dialyzate side of a module comprising about 10,000 hollow fiber membranes was filled with water and was then capped. A dry air or a nitrogen was fed from the blood side of the module at a room temperature so as to compress the module at a rate of 0.5 MPa/min. The pressure was increased until the hollow fiber membrane was burst by the compressed air. Then, the air pressure was measured, when bubbles occurred in the liquid filling the dialyzate side of the module, simultaneously with the bursting of the membrane. This air pressure was defined as a burst pressure.

4. Non-Uniformity in Thickness

The sections of 100 hollow fibers were observed with a projector of a magnification of 200. One hollow fiber which had the largest difference in thickness was selected in one field of view, and the thickest portion and the thinnest portion of the section of this hollow fiber were measured.

The non-uniformity in thickness=the thickness of the thinnest portion/the thickness of the thickest portion In this regard, the thickness of a membrane is perfectly uniform when the non-uniformity in thickness is one (=1).

5. Amount of Eluted Hydrophilic Polymer

A method of measuring the amount of polyvinyl pyrrolidone, as a hydrophilic polymer, eluted from a membrane is described.

<Dry Hollow Fiber Membrane Module>

A physiological saline was allowed to pass through the passage on the side a dialyzate in a module, at a rate of 500 mL/min. for 5 minutes, and then was allowed to pass through the passage on the side of blood, at a rate of 200 mL/minutes. After that, the physiological saline was allowed to pass from the side of blood to the side of the dialyzate at a rate of 200 mL/minute for 3 min. while being filtered.

<Wet Hollow Fiber Membrane Module>

The liquid was removed from a module, and the same operation as was done on the dry hollow fiber membrane module was carried out.

Extraction was made on the hollow fiber membrane module which had been subjected to the above priming treatment, according to the method regulated in the approved standards for manufacturing dialyzer type artificial kidney devices, and polyvinyl pyrrolidone in the extract was determined by a calorimetric method.

In detail, pure water (100 mL) was added to the hollow fiber membrane (1 g), and extraction was made on the hollow fiber membrane at 70° C. for one hour. The resultant extract (2.5 mL), a 0.2 mol aqueous citric acid solution (1.25 mL) and a 0.006N aqueous iodine solution (0.5 mL) were sufficiently mixed, and the mixture was left to stand alone at a room temperature for 10 minutes. After that, the absorbance of the mixture was measured at 470 nm. The determination was made using polyvinyl pyrrolidone as a sample, based on the analytical curve determined by the measurement according to the above method.

6. Contents of Hydrophilic Polymer in Uppermost Layers of Inner and Outer Surfaces of Membrane The content of a hydrophilic polymer was determined by the electron spectroscopy for chemical analysis (ESCA method). Analysis of polyvinyl pyrrolidone (PVP) as a hydrophilic polymer is herein explained.

One hollow fiber membrane was obliquely cut with a cutter so that a part of the inner surface of the membrane could be exposed, and the cut hollow fiber membrane was applied on a sample table so as to measure the inner and outer surfaces of the membrane. Then, the content of PVC was analyzed by the ESCA method. The conditions for the analysis were as follows:

Apparatus: ULVAC-PHI ESCA5800
Excitation X-ray: MgKα ray
X-ray output: 14 kV, 25 mA
Escape angle of photoelectron: 45°
Analysis diameter: 400 μmφ
Path energy: 29.35 eV
Resolution: 0.125 eV/step
Degree of vacuum: about $10^{-7}$ Pa or lower The content of PVP in the surface of the membrane was calculated from the found value of nitrogen (N) and the found value of sulfur (S), by the following equation.

<Membrane of PES (Polyethersulfone) Admixed with PVP>

Content of $PVP$ ($H_{pvp}$) [mass %]=100×(N×111)/(N× 111+S×232)

<Membrane of PSf (Polysulfone) Admixed with PVP>

Content of $PVP$ ($H_{pvp}$) [mass %]=100×(N×111)/(N× 111+S×442)

7. Content of Hydrophilic Polymer in a Whole of Hollow Fiber Membrane

Measurement of PVP as a hydrophilic polymer is described. A sample was dried with a vacuum drier at 80° C. for 48 hours, and 10 mg of the dried sample was analyzed with a CHN coder (Model MT-6, manufactured by YANAKO BUNSEKI KOGYOSHA). The content of PVP was calculated from the content of nitrogen by the following equation.

The content of PVP (mass %)=the content of nitrogen (mass %)×111/14

8. Content of Hydrophilic Polymer in Proximate Layer of Inner Surface of Hollow Fiber Membrane Measurement of PVP as a hydrophilic polymer is described. The measurement was conducted by an infrared absorbing analysis. A sample prepared in the same manner as in the above item 6 was used. The content of PVP in the proximate layer of the surface of the sample membrane was measured by the ATR method, and the content of PVP in a whole of the membrane was measured by the transmission method. In the ATR method, an infrared absorption spectrum was measured by using a diamond 45° as an internal reflecting element. Model IRμs/SIRM manufactured by SPECTRA TECH was used for the measurement. The ratio of the absorption intensity Ap of the peak derived from C=O of PVC at and around 1675 cm$^{-1}$ in the infrared absorption spectrum, to the absorption intensity As of the peak derived from a polysulfone-based polymer at and around 1580 cm$^{-1}$, i.e., Ap/As, was determined. In the ATR method, the absorption intensity depends on the measured wave number. Therefore, as a correction value, the ratio of the peak position vs of the polysulfone-based polymer and the peak position vp (wave number) of PVP, i.e., vp/vs was used for the measurement. The content of PVP in the proximate layer in the inner surface of the membrane was calculated by the following equation:

Content (mass %) of Hydrophilic Polymer in Proximate Layer of Surface of Membrane=$Cav \times Ap/As \times vp/vs$ In this equation, Cav is the content of PVP determined by "the method of the above item 7.

9. Ratio of Pore Areas of Outer Surface of Hollow Fiber Membrane

The outer surface of a hollow fiber membrane was observed with an electron microscope of a magnification of 10,000 and photographed (SEM photograph). The obtained image was processed with an image analysis processing soft to determine the ratio of pore areas of the outer surface of the hollow fiber membrane. For example, "Image Pro Plus" (Media Cybernetics, Inc.) was used as the image analysis processing soft for measurement. The fetched image was subjected to an emphasis and filter operation so as to discriminate the pore portions from the closed portions. After that, the number of the pores was counted. If polymer chains of the lower layer were observed in the interiors of the pores, such pores were combined and regarded as one pore. The area (A) of the measuring range and the total (B) of the areas of the pores within the measuring range were found to calculate the ratio of pore areas (%) by the following equation: the ratio of pore areas (%)=B/A×100. This calculation was repeated with respect to 10 fields of view, and an average of the results was found. Scale-setting was carried out as the initial operation, and the pores on the boundary around the measuring range were not excluded from the counting.

10. Average Pore Area of Void Portion of Outer Surface of Hollow Fiber Membrane

Counting was made in the same manner as in the above operation, to calculate the area of each pore. The pores on the boundary around the measuring range were excluded from the counting. This calculation was repeated with respect to 10 fields of view, and an average of all the pore areas was calculated.

11. Blood Leak Test

Bovine blood of 37° C. of which the coagulation was inhibited by the addition of citric acid was fed to a hollow fiber membrane module at a rate of 200 mL/min., and was filtered at a rate of 10 mL/(min.m$^2$). The resulting filtrate was returned to the blood to make a circulating system. After 60 minutes had passed, the filtrate of the hollow fiber membrane module was collected, and the reddish tone of the filtrate due to the leakage of blood cell was visually observed. This blood leak test was conducted on 30 hollow fiber membrane modules in each of Examples and Comparative Examples, and the number of modules from which blood leaked was counted.

12. Sticking of Hollow Fiber Membranes

About 10,000 hollow fiber membranes were bundled, and the bundle thereof was set in a module casing of 30 to 35 mmφ. The module casing was sealed with a two-component polyurethane resin to make up a module. The leak test was conducted on 5 standard modules. After that, the number of the modules from which the blood leaked due to the defect in the sealing with the urethane resin was counted.

13. Blood Residue in Hollow Fiber Membrane

The side of a dialyzate of a module having a membrane area of 1.5 m$^2$ was filled with physiological saline. A blood bag charged with 200 mL of heparinized blood collected from a healthy person was connected to the module through a tube, and the blood was allowed to circulate at a flow rate of 100 mL/minute at 37° C. for one hour. The blood was sampled before the start of circulation and after 60 minutes had passed since the start of circulation, respectively, to measure the number of white blood cells and the number of blood platelets. The measured values were corrected by hematocrit values.

Corrected value=Measured value (60 mins.)×Hematocrit (0 min.)/Hematocrit (60 mins.)

The rates of change in the amounts of the white blood cells and the blood platelets were calculated from the corrected value.

Rate of Change=Corrected value (60 mins.)/the value found before the start of circulation×100

After the completion of the circulation for 60 minutes, the blood was retransfused with a physiological saline, and the number of the hollow fiber membranes having the blood left to remain therein was counted. The evaluation criteria were based on the number of the hollow fiber membranes having the blood left to remain therein.

10 or less: ○
11 to 30: Δ
31 or more: X

14. Priming Capacity

Distilled water for injection was allowed to flow at a rate 200 mL/min. from the inlet port on the side of blood of a module, while the port on the side of a dialyzate was capped. The distilled water was degassed by lightly tapping the module casing 5 times with forceps for 10 seconds from the point of time when the distilled water had reached the outlet port. After that, the number of bubbles passing through for one minute was visually counted. The evaluation criteria were based on the number of bubbles observed:

10 or less/min.: ○
11 to less than 30/min.: Δ
30 or more/min.: X

15. Oxygen Concentration in Packaging Bag

The measurement was conducted by gas chromatography, using a column filled with a molecular sieve (13X-S mesh 60/80 manufactured by GL Science) and argon as a carrier gas. Detection was made by using a heat-conduction system, and an analysis was made at a column temperature of 60° C. A gas within a packaging bag was collected by directly pricking the closed packaging bag with a syringe needle.

16. Relative Humidity within Packaging Bag

The sensor probe of a temperature- and humidity-measuring instrument (ONDOTORI® PH Type manufactured by T&D) was inserted into a packaging bag to measure the relative humidity within the bag.

17. Amount of Eluted Hydrogen Peroxide

A liquid (2.6 mL) extracted from a membrane by the method regulated in the UV absorptionmetry (220 to 350 nm) in the approved standards for manufacturing dialyzer type artificial kidney devices was admixed with an ammonium chloride buffer solution (pH 8.6) (0.2 mL) and a 0.4 mM coloring reagent (0.2 mL) prepared by mixing titanium tetrachloride (a hydrogen chloride solution) and 4-(2-pyridylazo) resorcinol.sodium salt (an aqueous solution) in equivalent amounts in molar ratio. The mixture was heated at 50° C. for 5 minutes, and then was cooled to a room temperature and was subjected to an absorptionmetry at 508 nm. Determination was made by using an analytical curve which was prepared by measuring an absorbance of a sample in the same manner.

18. Oxygen Permeability of Packaging Material

An oxygen permeability-measuring apparatus (OX-TO-RAN 100 manufactured by Modern Controls) was used to measure the oxygen permeability of the material of the packaging bag at 20° C. and 90% RH.

19. Water Vapor Permeability of Packaging Material

A water vapor permeability-measuring apparatus (PAR-MATRAN-W manufactured by Modern Controls) was used to measure the waver vapor permeability of the material of the packaging bag at 40° C. and 90% RH.

20. Amount of Consumed Potassium Permanganate

A physiological saline was allowed to pass through a hollow fiber membrane module at a flow rate of 100 mL/min. and filled the same. Then, 25 ml of a washing liquid which flowed out for 15 seconds immediately after the filling of the module was collected. Ten mL of this washing liquid was sampled and admixed with an aqueous solution of potassium permanganate ($2.0 \times 10^{-3}$ mol/L) (20 mL) and diluted hydrochloric acid (1 mL). The mixture was boiled for 3 minutes and then was cooled to a room temperature. To the resulting solution was added an aqueous potassium iodide solution (1 mL), and the mixture was sufficiently stirred and then was left to stand for 10 minutes. Then, the resulting solution was subjected to titration using an aqueous solution of sodium thiosulfate ($1.0 \times 10^{-2}$ mol/L). A difference was found between the amount of the aqueous solution of sodium thiosulfate used for the titration of a physiological saline which was not allowed to pass through the module and the amount of the aqueous solution of sodium thiosulfate used for the titration of the initial washing liquid, and this difference in amount was defined as the amount of the aqueous solution of potassium permangnoate consumed by the eluted substance (the amount of the consumed aqueous potassium permangnoate solution).

21. Moisture Content

To find a moisture content (mass %), the mass (a) of a hollow fiber membrane before dried and the mass (b) of the same hollow fiber membrane after dried at 120° C. in an oven for 2 hours (bone-dried) were measured. The moisture content was calculated by the following equation:

Moisture content (mass %)=$(a-b)/b \times 100$ wherein, if (a) is from 1 to 2 g, the hollow fiber membrane could be bone-dried in 2 hours (if bone-dried, the membrane shows no further change in mass).

Example 1

Polyethersulfone (SUMIKAEXCEL®4800P, manufactured by Sumika Chem Tex Co., Ltd.) (17.6 mass %), polyvinyl pyrrolidone (KOLLIDONE®K-90 manufactured by BASF) (4.8 mass %), dimethylacetamide (DMAc) (74.6 mass %) and water (3 mass %) were homogeneously dissolved at 50° C., and then, the system was decompressed to −500 mmHg with a vacuum pump. After that, the system was immediately sealed so as not to change the composition of the membrane-forming solution due to the evaporation of the solvent or the like, and the system was left to stand alone for 15 minutes. This operation was repeated three times to degas the membrane-forming solution. This solution was allowed to pass through three-staged sintered filters with pore sizes of 15 µm, 15 µm and 15 µm in this order, and then was extruded from the outer slit of a tube-in-orifice nozzle heated to 65° C. Simultaneously with this extrusion, an aqueous solution of DMAc (45 mass %) of 15° C. as an interior-coagulating solution which had been previously degassed for 60 minutes under a pressure of −700 mmHg was extruded from the hole for an inner solution. Then, the semi-solid hollow fiber membrane was allowed to pass through a drying zone with a length of 450 mm, which was shielded from an external air by a spinning tube, and then was coagulated in an aqueous solution of DMAc (20 mass %) of 60° C. The resultant membrane in a wet state was directly wound onto a hank. The slit of the tube-in-orifice nozzle used had an average width of 60 µm, a maximum width of 61 µm and a minimum width of 59 µm, and the ratio of the maximum value to the minimum value of the width of the slit was 1.03. The draft ratio of the membrane-forming solution was 1.1. The rollers used, with which the hollow fiber membranes came into contact during the spinning step, were planished at their surfaces, and all the guides used were matte-finished at their surfaces.

A bundle of about 10,000 hollow fiber membranes as obtained above was wrapped in a polyethylene film which was matte-finished at its surface on the side of the bundle, and then was cut into bundles of the hollow fiber membranes with lengths of 27 cm. These bundles were washed in hot water of 80° C. for 30 minutes. This washing was repeated 4 times. The bundles of the wet membranes were subjected to centrifugal dehydration at 600 rpm for 5 minutes, and each 12 bundles of the membranes were set on each of two-staged turn tables in the drying apparatus and were exposed to microwaves of initial 1.5 kW with a microwave-generating apparatus in which reflecting plates were provided in the oven for uniform heating. Simultaneously with this operation, the interior space of the drying apparatus was decompressed to 7 kPa with a vacuum pump, so as to dry the bundles of membranes for 28 minutes. Sequentially, the bundles of membranes were dried under the application of microwaves with an output of 0.5 kW and under reduced pressure 7 kPa for 12 minutes. The output of microwave was decreased to 0.2 kW, under which the bundles of membranes were similarly dried for 8 minutes. Thus, the drying of the bundles of membranes was completed. Infrared exposure was concurrently carried out in combination with the microwave exposure. The highest temperature of the surface of the bundle of membranes at this step was 65° C., and the moisture content of the dried hollow fiber membrane was 2.1 mass % on average. The inner diameter of the hollow fiber membrane was 199.4 µm, and the thickness thereof was 28.6

A hollow fiber membrane module was made up of the hollow fiber membranes thus obtained, and was subjected to a leak test. As a result, no failure in adhesion, attributed to the sticking of the hollow fiber membranes, was observed. Further, the PVP contents in the uppermost layer and the proximate layer of the inner surface of the hollow fiber membrane, the PVP content in the uppermost layer of the outer surface of the hollow fiber membrane and the PVP content in a whole of the hollow fiber membrane were measured. The results are shown in Table 1.

The hollow fiber membrane module was sealed in a packaging bag made of an aluminum lamination sheet which comprised an outer layer of a polyester film, an intermediate layer of an aluminum foil and an inner layer of a polyethylene film and which had an oxygen permeability of 0.5 cm$^3$/ (m$^2$0.24 h.atm) and a water vapor permeability of 0.5 g/(m$^2$0.24 h.atm), together with two moisture-releasing type oxygen scavengers (Ageless® Z-200PT manufactured by Mitsubishi Gas Chemical Company, Inc.). A plurality of such packaging bags including the hollow fiber membrane modules, respectively, were prepared, and then were sealed and stored at room temperatures for 2 days. After that, one of the packaging bags was subjected to the measurement of its oxygen concentration and humidity and to the measurement of the moisture content of the hollow fiber membrane therein. The rest of the packaging bags were exposed to γ-rays of 25 kGy. The oxygen concentrations and humidities within these packaging bags and the moisture contents of the hollow fiber membranes were measured after the γ-ray exposure. The hollow fiber membrane modules were removed from the packaging bags exposed to γ-rays, and the amounts of consumed potassium permanganate were measured. The results are shown in Table 2. In the meantime, the packaging bags exposed to γ-rays were stored at room temperatures for 3 months, and then, the amounts of hydrogen peroxide eluted from the hollow fiber membranes were measured. The results are shown in Table 2.

Fresh bovine blood admixed with citric acid was allowed to pass through a blood purifier at a flow rate of 200 mL/min. and at a filtering rate of 10 mL/(min.m$^2$). As a result, no leakage of blood cells was observed. The amount of endotoxin filtered from the outside of the hollow fiber membrane to the inside thereof was smaller than the limit for detection, which was in the level of no problem. The results of other analyses are shown Table 1.

TABLE 1

Part 1

|  | Ex. 1 | Ex. 2 | Ex. 3 | Ex. 4 |
|---|---|---|---|---|
| PVP content [A] in uppermost layer of inner surface of membrane (mass %) | 24 | 22 | 34 | 29 |
| PVP content [B] in proximate layer of inner surface of membrane (mass %) | 12 | 13 | 16 | 18 |
| PVP content [C] in uppermost layer of outer surface of membrane (mass %) | 35 | 26 | 38 | 39 |
| [A]/[B] | 2.00 | 1.69 | 2.13 | 1.61 |
| [C]/[A] | 1.46 | 1.18 | 1.12 | 1.34 |
| PVP content in a whole of membrane (mass %) | 3.4 | 3.8 | 7.5 | 3.8 |
| Water permeability (mL/m$^2$/hr/mmHg) | 578 | 380 | 631 | 422 |
| Burst pressure (MPa) | 0.7 | 0.7 | 1.0 | 1.0 |
| Non-uniformity in thickness (ratio) | 0.78 | 0.88 | 0.86 | 0.88 |
| Blood leakage (number of membranes) | 0 | 0 | 0 | 0 |
| Amount of eluted PVP (ppm) | 5 | 6 | 9 | 5 |
| Average pore area of outer surface of membrane (μm$^2$) | 0.7 | 0.6 | 0.9 | 0.7 |
| Percentage of pore areas of outer surface of membrane (%) | 19 | 20 | 13 | 21 |
| Moisture content of dried membrane (mass %) | 2.1 | 2.8 | 1.8 | 1.6 |
| PVP/PSf in dope | 0.27 | 0.28 | 0.49 | 0.28 |
| Number of stuck membranes | 0 | 0 | 0 | 0 |
| Endotoxin permeability (%) | <0.01 | <0.01 | <0.01 | <0.01 |
| Blood residue | ○ | ○ | ○ | ○ |
| Priming | ○ | ○ | ○ | ○ |

Part 2

|  | C. Ex. 1 | C. Ex. 2 | C. Ex. 3 | C. Ex. 4 | C. Ex. 5 |
|---|---|---|---|---|---|
| PVP content [A] in uppermost layer of inner surface of membrane (mass %) | 19 | 44 | 39 | 28 | — |
| PVP content [B] in proximate layer of inner surface of membrane (mass %) | 4 | 26 | 20 | 10 | — |
| PVP content [C] in uppermost layer of outer surface of membrane (mass %) | 20 | 40 | 24 | 57 | — |
| [A]/[B] | 4.75 | 1.69 | 1.95 | 2.80 | — |
| [C]/[A] | 1.05 | 0.91 | 0.62 | 2.04 | — |
| PVP content in a whole of membrane (mass %) | 2.4 | 13.2 | 8.8 | 10.4 | — |
| Water permeability (mL/m$^2$/hr/mmHg) | 560 | 340 | 366 | — | 1260 |
| Burst pressure (MPa) | 0.7 | 0.7 | 0.6 | — | 0.8 |

TABLE 1-continued

| | | | | | |
|---|---|---|---|---|---|
| Non-uniformity in thickness (ratio) | 0.78 | 0.71 | 0.69 | — | 0.87 |
| Blood leakage (number of membranes) | 0 | 0 | 0 | — | 0 |
| Amount of eluted PVP (ppm) | 6 | 20 | 10 | 13 | — |
| Average pore area of outer surface of membrane ($\mu m^2$) | 0.5 | 0.3 | 0.4 | 0.2 | 0.1 |
| Percentage of pore areas of outer surface of membrane (%) | 20 | 10 | 11 | 6 | 8 |
| Moisture content of dried membrane (mass %) | 3.5 | 4.6 | 2.6 | 1.9 | 0.6 |
| PVP/PSf in dope | 0.27 | 0.68 | 0.68 | 0.30 | — |
| Number of stuck membranes | 0 | 4 | 0 | 5 | 0 |
| Endotoxin permeability (%) | <0.01 | 0.031 | <0.01 | — | <0.01 |
| Blood residue | x | ○ | ○ | — | x |
| Priming | ○ | ○ | x | — | x |

TABLE 2

Part 1

| | Ex. 1 | Ex. 2 | Ex. 3 | Ex. 4 |
|---|---|---|---|---|
| Moisture content (mass %) of membrane during γ-ray exposure | 1.8 | 2.4 | 1.6 | 1.6 |
| Humidity (% RH) during γ-ray exposure | 72 | 74 | 62 | 68 |
| Oxygen concentration (%) during γ-ray exposure | <0.01 | <0.01 | <0.01 | <0.01 |
| Amount of consumed potassium permanganate ($mL/m^2$) after γ-ray exposure | 0.9 | 1.9 | 2.4 | 1.2 |
| Amount of hydrogen peroxide eluted from membrane after 3 months from γ-ray exposure (ppm) | ND | 1 | 1 | ND |

Part 2

| | C. Ex. 1 | C. Ex. 2 | C. Ex. 3 | C. Ex. 5 | C. Ex. 6 | C. Ex. 7 | C. Ex. 8 |
|---|---|---|---|---|---|---|---|
| Moisture content (mass %) of membrane during γ-ray exposure | 3.2 | 4.2 | 2.5 | 0.2 | 2.0 | 1.9 | 1.9 |
| Humidity (% RH) during γ-ray exposure | 39 | 37 | 36 | 34 | 48 | 41 | 51 |
| Oxygen concentration (%) during γ-ray exposure | <0.01 | <0.01 | <0.01 | <0.01 | 24 | <0.01 | 25 |
| Amount of consumed potassium permanganate ($mL/m^2$) after γ-ray exposure | 2.6 | 6.2 | 3.1 | 1.1 | 10.9 | 2.5 | 11.2 |
| Amount of hydrogen peroxide eluted from membrane after 3 months from γ-ray exposure (ppm) | 11 | 12 | 10 | 7 | 70 | 11 | 20 |

Comparative Example 1

Wet hollow fiber membranes were obtained in the same manner as in Example 1, except that the amounts of polyvinyl pyrrolidone (KOLLIDONE®K-90 manufactured by BASF) and DMAc of a spinning dope were changed to 2.4 mass % and 77 mass %, respectively, and that a drying zone with a length of 700 mm was used. The resultant hollow fiber membranes were washed in the same manner as in Example 1, and dried in a hot air drier of 60° C. The moisture content of the resultant hollow fiber membrane was 3.4 mass %, and the inner diameter thereof was 199.6 µm, and the thickness thereof was 29.7 µm. The hollow fiber membrane module was exposed to γ-ray in the same manner as in Example 1, except that an oxygen scavenger which was not of moisture-releasing type (TAMOTSU® manufactured by OJITAC) was used. The characteristics of the resultant hollow fiber membrane and the resultant hollow fiber membrane bundle are shown in Tables 1 and 2. The hollow fiber membranes of Comparative Example 1 had the blood left to remain therein. This was because the content of PVP in the proximate layer of the inner surface of the membrane was low. In addition, the humidity within the bag could not be controlled, since the oxygen scavenger which was not of moisture-releasing type was used in Comparative Example 1. Thus, the hollow fiber membrane module was exposed to γ-ray at a lower humidity, which, it was supposed, led to a larger amount of eluted hydrogen peroxide.

Comparative Example 2

A spinning dope was obtained in the same manner as in Example 1, except that the amount of PVP (KOLLIDONE®K-90 manufactured by BASF) was changed to 12.0 mass %, and the amount of DMAc, to 67.4 mass %. Further, hollow fiber membranes and a hollow fiber membrane module were obtained in the same manners as in Example 1, except that the temperature of the void-forming agent was not controlled, that the hollow fiber membranes were not washed, that the bundle of hollow fiber membranes was dried in the same manner as in Comparative Example 1, and that the hollow fiber membrane module was exposed to γ-ray in the same manner as in Comparative Example 1. The characteristics of the resultant hollow fiber membranes and the resultant hollow fiber membrane module are shown in Tables 1 and 2. The hollow fiber membrane obtained in Comparative Example 2 had a higher content of PVP in the uppermost layer of the inner surface thereof, and the amount of eluted PVA was larger. In addition, the permeation of endotoxin into the blood side was observed because of the higher content of PVP in the outer surface of the hollow fiber membrane. Also, in Comparative Example 2, the humidity within the bag was not controlled, and thus, the hollow fiber membrane module was exposed to γ-ray at a lower humidity, which led to a larger amount of eluted hydrogen peroxide.

Comparative Example 3

Hollow fiber membranes and a hollow fiber membrane module were obtained in the same manners as in Comparative Example 2, except that the hot water washing was repeated 6 times. The characteristics of the resultant hollow fiber membranes and the resultant hollow fiber membrane module are shown in Tables 1 and 2. The hollow fiber membrane bundle obtained in Comparative Example 3 had a lower content of PVP in the uppermost layer of the outer surface thereof, and thus, the priming capacity was inferior because of the lower hydrophilicity of the outer surface thereof. Also, in Comparative Example 3, the humidity within the bag was not controlled, and thus, the hollow fiber membrane module was exposed to γ-ray at a lower humidity, which led to a larger amount of eluted hydrogen peroxide.

Example 2

Polyethersulfone (SUMIKAEXCEL®4800P, manufactured by Sumika Chem Tex Co., Ltd.) (18.8 mass %), polyvinyl pyrrolidone (KOLLIDONE®K-90 manufactured by BASF) (5.2 mass %), DMAc (71.0 mass %) and water (5 mass %) were dissolved at 50° C., and then, the system was decompressed to −700 mmHg with a vacuum pump. After that, the system was immediately sealed so as not to change the composition of the membrane-forming solution due to the evaporation of the solvent or the like, and the system was left to stand for 10 minutes. This operation was repeated three times so as to degas the membrane-forming solution. This solution was allowed to pass through filters with pore sizes of 15 μm and 15 μm in two stages, and then was extruded from the outer slit of a tube-in-orifice nozzle heated to 70° C. Simultaneously with this extrusion, an aqueous solution of DMAc (55 mass %) of 10° C. as an interior-coagulating solution which had been previously degassed for 2 hours under a pressure of −700 mmHg was extruded from the inner hole of the nozzle. The resultant hollow fiber membrane was allowed to pass through an air gap with a length of 330 mm, which was blocked from an external air by a spinning tube, and then was coagulated in water of 60° C. The slit of the tube-in-orifice nozzle used had an average width of 45 μm, a maximum width of 45.5 μm and a minimum width of 44.5 μm, and the ratio of the maximum value to the minimum value of the width of the slit was 1.02. The draft ratio was 1.1. The absolute humidity of the drying zone was 0.12 kg/kg in a dry air. The hollow fiber membrane removed from the coagulation bath was allowed to pass through a water bath of 85° C. for 45 seconds to remove the solvent and the excessive hydrophilic polymer, and then was wound up. A bundle of about 10,000 hollow fiber membranes as obtained above was wrapped in the same polyethylene film as that used in Example 1, and then was immersed in an aqueous solution of 40 vol. % of isopropanol of 30° C. for 30 minutes. This immersion was repeated twice, and this aqueous solution was replaced with water. The rollers used for changing the fiber path in the spinning step were planished at their surfaces, and the stationary guides used were matte-finished at their surfaces.

The bundle of the wet hollow fiber membranes was subjected to centrifugal dehydration at 600 rpm for 5 minutes, and each 48 bundles of the membranes were set on each of turn tables in two stages in a drying apparatus and were then exposed to microwaves of initial 7 kW. Simultaneously with this operation, the interior space of the drying apparatus was decompressed to 5 kPa so as to dry the bundles of membranes fro 65 minutes. Sequentially, the bundles of membranes were dried under the application of microwaves with an output of 3.5 kW and under reduced pressure of 5 kPa for 50 minutes. The output of microwave was decreased to 2.5 kW, under which the bundles of membranes were similarly dried for 10 minutes. Thus, the drying of the bundles of membranes was completed. The highest temperature of the surface of the bundle of membranes at this drying treatment was 65° C., and the moisture content of the dried hollow fiber membrane was 2.8 mass % on average. The inner diameter of the hollow fiber membrane was 200.2 μm, and the thickness thereof was 28.0

A hollow fiber membrane module was made up of the hollow fiber membranes thus obtained, and was subjected to a leak test. As a result, no failure in adhesion, attributed to the sticking of the hollow fiber membranes, was observed. Further, the PVP contents in the uppermost layer and the proximate layer of the inner surface of this hollow fiber membrane, the PVP content in the uppermost layer of the outer surface of the hollow fiber membrane and the PVP content in a whole of the hollow fiber membrane were measured. The results are shown Table 1.

The hollow fiber membrane module was subjected to γ-ray exposure and various analyses in the same manners as in Example 1. The results are shown in Tables 1 and 2.

In a blood leak test using bovine blood, no leakage of blood cells was observed. As a result of an endotoxin permeation test, the amount of the endotoxin filtered from the outside of the hollow fiber membrane to the inside thereof was smaller than the limit for detection, which was in the level of no problem.

Comparative Example 4

Polyethersulfone (SUMIKAEXCEL®7800P, manufactured by Sumika Chem Tex Co., Ltd.) (23 mass %), PVP (KOLLIDONE®K-30 manufactured by BASF) (7 mass %), DMAc (67 mass %) and water (3 mass %) were dissolved at 50° C., and then, the system was decompressed to −500 mmHg with a vacuum pump. After that, the system was immediately sealed so as not to change the composition of the membrane-forming solution due to the evaporation of the solvent or the like, and the system was left to stand alone for 30 minutes. This operation was repeated twice so as to degas the membrane-forming solution. This solution was allowed to pass through filters with pore sizes of 30 μm and 30 μm in two stages, and then was extruded from the outer slit of a tube-in-orifice nozzle heated to 50° C. Simultaneously with this extrusion, an aqueous solution of DMAc (50 mass %) of 50° C. as an interior-coagulating solution which had been previously degassed under reduced pressure was extruded from the inner hole of the nozzle. The semi-solid hollow fiber membrane was allowed to pass through an air gap with a length of 350 mm, which was blocked from an external air with a spinning tube, and then was coagulated in water of 50° C. The slit of the tube-in-orifice nozzle used had an average width of 45 μm, a maximum width of 45.5 μm and a minimum width of 44.5 μm, and the ratio of the maximum value to the minimum value of the width of the slit was 1.02. The draft ratio of the membrane-forming solution was 1.1. The absolute humidity of the drying zone was 0.07 kg/kg in a dry air. The hollow fiber membrane removed from the coagulation bath was allowed to pass through a water bath of 85° C. for 45 seconds to remove the solvent and the excessive hydrophilic polymer, and then was wound up. A bundle of 10,000 hollow fiber membranes as obtained above was directly dried at 60° C. for 18 hours, without washing. Sticking of the dried hollow fiber membranes was observed. It was impossible to make up a blood purifier of the hollow fiber membranes thus obtained, since an adhesive resin could not be successfully inserted between each of the hollow fiber membranes, when making up the blood purifier. The results of the analyses are shown Table 1.

Comparative Example 5

Polyethersulfone (SUMIKAEXCEL®4800P, manufactured by Sumika Chem Tex Co., Ltd.) (20 mass %), triethyleneglycol (manufactured by MISTUI CHEMICALS, INC.) (40 mass %), and N-methyl 2-pyrrolidone (manufactured by Mitsubishi Chemical Corporation) (40 mass %) were mixed and stirred to prepare a homogeneous and transparent membrane-forming solution. A hollow fiber membrane was obtained in the same manner as in Example 2, except that this membrane-forming solution and N-methyl 2-pyrrolidone/triethyleneglycol/water (=5/5/90) as a void-forming material were used. The inner diameter of the hollow fiber membrane was 194.8 μm; the thickness thereof was 50.5 μm; the moisture content thereof was 0.4 mass %; and the content of a hydrophilic polymer to the content of the hydrophobic polymer was 0 mass %. A module of such hollow fiber membranes was exposed to γ-ray in the same manner as in Comparative Example 1. The characteristics of the resultant hollow fiber membrane and the resultant hollow fiber membrane module are shown in Tables 1 and 2.

The hollow fiber membranes showed no sticking thereof and no backflow of endotoxin, but could not be used as a membrane for hemodialysis. The reasons therefor were that the hollow fiber membrane showed strong hydrophobic properties because of containing no hydrophilic polymer, and that the protein in blood clogged the pores of the membrane and was accumulated on the surface of the membrane.

Example 3

Polysulfone (P-3500 manufactured by AMOCO) (18.5 mass %), polyvinyl pyrrolidone (K-60 manufactured by BASF) (9 mass %), DMAc (67.5 mass %) and water (5 mass %) were dissolved at 50° C. Then, the inner space of the system was decompressed to −300 mmHg with a vacuum pump, and then was immediately sealed so as not to change the composition of the membrane-forming solution due to the evaporation of the solvent or the like and left to stand alone for 15 minutes. This operation was repeated three times to degas the membrane-forming solution. The resultant membrane-forming solution was allowed to pass through filters with pore sizes of 15 μm and 15 μm in two stages, and then was extruded through the outer slit of a tube-in-orifice nozzle heated to 40° C. Simultaneously with this extrusion, an aqueous solution of 35 mass % of DMAc of 0° C. as a void-forming agent which had been previously degassed under reduced pressure was extruded through the inner hole of the tube-in-orifice nozzle. The semi-solid hollow fiber membrane was allowed to pass through an air gap with a length of 600 mm which was shielded from an external air by a spinning tube, and then was coagulated in water of 50° C. The slit of the tube-in-orifice nozzle had an average width of 60 μm, a maximum width of 61 μm and a minimum width of 59 μm; the ratio of the maximum value to the minimum value of the width of the slit was 1.03; the draft ratio was 1.1; and the absolute humidity of the drying zone was 0.06 kg/kg in a dry air. The hollow fiber membrane removed from the coagulation bath was allowed to pass through a water bath of 85° C. for 45 seconds so as to remove the solvent and the excessive hydrophilic polymer, and then was wound up. A bundle of 10,500 hollow fiber membranes thus obtained was immersed in pure water, and then washed in an autoclave at 121° C. for one hour. After the washing, the bundle of hollow fiber membranes was wrapped in the same polyethylene film as that used in Example 1, and then was dried in the same manner as in Example 1. The rollers used for changing the fiber path in the spinning step were planished at their surfaces, and the stationary guides were matt-finished at their surfaces. The inner diameter of the resultant hollow fiber membrane was 200.8 μm, and the thickness thereof was 44.4 μm.

The hollow fiber membranes thus obtained were used to make up a hollow fiber membrane module, which was then subjected to a leak test. As a result, no failure in adhesion due to the sticking of the hollow fiber membranes was observed. The PVP contents in the uppermost layer and the proximate layer of the inner surface of this hollow fiber membrane, the PVP content in the uppermost layer of the outer surface of the same membrane, and the PVP content in a whole of the same membrane were measured. The results are shown in Table 1. The hollow fiber membrane module was exposed to γ-ray in the same manner as in Example 1.

Fresh bovine blood admixed with citric acid was allowed to pass through the blood purifier at a flow rate of 200 mL/min. and at a filtering rate of 10 mL/(min.m$^2$), with the result that no leakage of red blood cells was observed. The amount of endotoxin filtered from the outer side to the inner side of the hollow fiber membrane was smaller than the limit for detection, which was in the level of no problem. The results of other analyses are shown in Tables 1 and 2.

Example 4

Polysulfone (P-1700 manufactured by AMOCO) (17 mass %), polyvinyl pyrrolidone (K-60 manufactured by BASF) (4.8 mass %), DMAc (73.2 mass %) and water (5 mass %) were dissolved at 50° C. The inner space of the system was decompressed to −400 mmHg with a vacuum pump, and then was immediately sealed so as not to change the composition of the membrane-forming solution due to the evaporation of the solvent or the like, and was left to stand for 30 minutes. This operation was repeated three times to degas the membrane-forming solution. The resultant membrane-forming solution was allowed to pass through two-stepped filters with pore sizes of 15 μm and 15 μm, and then was extruded through the outer slit of a tube-in-orifice nozzle heated to 40° C. Simultaneously with this extrusion, an aqueous solution of 35 mass % of DMAc of 0° C. as an interior-coagulating solution which had been previously degassed under reduced pressure was extruded through the inner hole of the tube-in-orifice nozzle. The semi-solid hollow fiber membrane was allowed to pass through an air gap with a length of 600 mm which was shielded from an external air by a spinning tube, and then was coagulated in water of 50° C. The slit of the tube-in-orifice nozzle had an average width of 60 μm, a maximum width of 61 μm and a minimum width of 59 μm; the ratio of the maximum value to the minimum value of the width of the slit was 1.03; the draft ratio was 1.1; and the absolute humidity of the drying zone was 0.07 kg/kg in a dry air. The hollow fiber membrane removed from the coagulation bath was allowed to pass through a water bath of 85° C. for 45 seconds so as to remove the solvent and the excessive hydrophilic polymer, and then was wound up. A bundle of 10,700 hollow fiber membranes thus obtained was immersed in pure water, and was then washed in an autoclave at 121° C. for one hour. After the washing, the bundle of hollow fiber membranes was wrapped in a polyethylene film, and then was dried in the same manner as in Example 2. The rollers used for changing the fiber path in the spinning step were planished at their surfaces, and the stationary guides were matt-finished at their surfaces. The inner diameter of the resultant hollow fiber membrane was 201.6 μm, and the thickness thereof was 44.2 μm.

The bundle of the hollow fiber membranes thus obtained was used to make up a hollow fiber membrane module, which was then subjected to a leak test. As a result, no failure in adhesion due to the sticking of the hollow fiber membranes was observed. The PVP contents in the uppermost layer and the proximate layer of the inner surface of this hollow fiber membrane, the PVP content in the uppermost layer of the outer surface of the same membrane, and the PVP content in a whole of the same membrane were measured. The results are shown in Table 1. The hollow fiber membrane module was exposed to γ-ray in the same manner as in Example 1.

Fresh bovine blood admixed with citric acid was allowed to pass through the blood purifier at a flow rate of 200 mL/min. and at a filtering rate of 10 mL/(min.m²), with the result that no leakage of red blood cells was observed. The amount of endotoxin filtered from the outer side to the inner side of the hollow fiber membrane was smaller than the limit for detection, which was in the level of no problem. The results of other analyses are shown in Tables 1 and 2.

Comparative Example 6

A hollow fiber membrane module was made up of the hollow fiber membranes of Example 1, and then was exposed to γ-ray in the same manner as in Example 1, except that no oxygen scavenger was used. The characteristics of the resultant hollow fiber membranes and the resultant hollow fiber membrane module are shown in Table 2. Since no oxygen scavenger was used in Comparative Example 6, the humidity in the packaging bag could not be controlled, and the oxygen concentration in the packaging bag could not be decreased. Thus, the hollow fiber membrane module was exposed to γ-ray under an ambient atmosphere of a low humidity and a high oxygen concentration. For this reason, the amount of consumed potassium permangnate and the amount of eluted hydrogen peroxide were both increased.

Comparative Example 7

A hollow fiber membrane module was made up of the hollow fiber membranes of Example 1, and then was exposed to y-ray in the same manner as in Example 1, except that an oxygen scavenger (TAMOTSU® manufactured by OJITAC) which was not of moisture-releasing type was used. The characteristics of the resultant hollow fiber membrane and the resultant hollow fiber membrane module are shown in Table 2. Since the oxygen scavenger used in Comparative Example 7 was not of moisture-releasing type, the humidity in the packaging bag could not be controlled, and thus, the hollow fiber membrane module was exposed to g-ray under an ambient atmosphere of a low humidity. For this reason, the amount of eluted hydrogen peroxide was increased.

Comparative Example 8

A hollow fiber membrane module was made up of the hollow fiber membranes of Example 1, and then was exposed to γ-ray in the same manner as in Example 1, except that an EOG sterilized bag which permitted a gas to freely permeate itself was used. The characteristics of the resultant hollow fiber membrane and the resultant hollow fiber membrane module are shown in Table 2. Since the bag which permitted a gas to freely permeate itself was used in Comparative Example 8, the humidity in the packaging bag could not be controlled, and the oxygen concentration in the packaging bag could not be decreased. Thus, the hollow fiber membrane module was exposed to γ-ray under an ambient atmosphere of a low humidity and a high oxygen concentration. For this reason, the amount of consumed potassium permanganate and the amount of eluted hydrogen peroxide were both increased.

INDUSTRIAL APPLICABILITY

The hollow fiber membrane modules of the present invention are highly reliable in safety and performance stability, having high water permeability suitable for use in the therapy of renal failures. The hollow fiber membrane modules of the present invention can be used in dry states, and thus are light in weight and are free of a possibility of being frozen. Therefore, the hollow fiber membrane modules of the present invention can be suitably used as blood purifiers which are easy to handle and exhibit high performance. Also, the hollow fiber membrane modules of the present invention are capable of inhibiting the infiltration of eluted substances which are foreign matter to human bodies, and thus are safe as medical devices. Therefore, the hollow fiber membrane modules of the present invention are suitable for use as blood purifiers, and will contribute much to the industrial field.

The invention claimed is:

1. A hollow fiber membrane module comprising polysulfone type selectively permeable hollow fiber membranes which contain a polysulfone -based resin and a hydrophilic polymer as main components, wherein
   (A) the content of the hydrophilic polymer in the uppermost layer of the inner surface of said hollow fiber membrane is at least 1.1 times larger than the content of the hydrophilic polymer in the proximate layer of the inner surface of said hollow fiber membrane,
   (B) the content of the hydrophilic polymer in the uppermost layer of the outer surface of said hollow fiber membrane is at least 1.1 times larger than the content of the hydrophilic polymer in the uppermost layer of the inner surface of said hollow fiber membrane, and
   (C) said hollow fiber membrane module is exposed to a radioactive ray while said hollow fiber membrane module is sealed in a packaging bag, on condition that the oxygen concentration of an ambient atmosphere within the packaging bag around said hollow fiber membrane is from 0.001 to 0.1%, and that the moisture content of said hollow fiber membrane to the weight thereof is from 0.2 to 7 mass %,
   wherein the uppermost layer of the inner surface of said hollow fiber membrane is a layer having a depth of up to 10 nm from the inner surface of the hollow fiber membrane, and the proximate layer of the inner surface of said hollow fiber membrane is a layer having a depth of from 1,000 to 1,500 nm from the inner surface of the hollow fiber membrane.

2. The hollow fiber membrane module according to claim 1, wherein said radiation exposure is done under an internal atmosphere of said bag, of which the relative humidity is higher than 40% RH at 25° C.

3. The hollow fiber membrane module according to claim 1, wherein said radiation exposure is done after at least 10 hours has passed since an oxygen scavenger was put in the packaging bag.

4. The hollow fiber membrane module according to claim 3, wherein said oxygen scavenger has a function to release a moisture content.

5. The hollow fiber membrane module according to claim 1, wherein said packaging bag is made of a material which shuts out an external air and a water vapor.

6. The hollow fiber membrane module according to claim 1, wherein the oxygen permeability of said packaging bag is not larger than 1 cm$^3$/(m$^2$0.24h.atm) (20° C. and 90% RH).

7. The hollow fiber membrane module according to claim 1, wherein the water vapor permeability of said packaging bag is not larger than 5 g/(m$^2$0.24h.atm) (40° C. and 90% RH).

8. The hollow fiber membrane module according to claim 1, wherein the inner atmosphere of said packaging bag and/or the ambient atmosphere of said hollow fiber membrane are/is of an inert gas.

9. The hollow fiber membrane module according to claim 1, wherein the amount of an aqueous solution of potassium permanganate (2.0×10$^{-3}$ mol/L) consumed for the titration of an eluted substance in 10 mL of an initial washing liquid from the hollow fiber membrane module after the radiation exposure is not larger than 5 mL per 1 m$^2$ of the inner surface of the hollow fiber membrane.

10. The hollow fiber membrane module according to claim 1, wherein the amount of hydrogen peroxide eluted from the hollow fiber membrane which is removed from the hollow fiber membrane module after at least 3 months has passed since the radiation exposure is not larger than 10 ppm.

11. The hollow fiber membrane module according to claim 1, wherein the content of the hydrophilic polymer in the polysulfone type hollow fiber membrane is 20 to 40 mass % in the uppermost layer of the inner surface, 5 to 20 mass % in the proximate layer thereof, and 25 to 50 mass % in the uppermost layer of the outer surface.

12. The hollow fiber membrane module according to claim 1, which comprises 99 to 80 mass % of the polysulfone-based resin and 1 to 20 mass % of the hydrophilic polymer as main components.

13. The hollow fiber membrane module according to claim 1, wherein said hydrophilic polymer is polyvinyl pyrrolidone.

14. The hollow fiber membrane module according to claim 1, wherein the amount of the hydrophilic polymer eluted from the hollow fiber membrane is not larger than 10 ppm.

15. The hollow fiber membrane module according to claim 1, wherein the ratio of pore areas of the outer surface of the hollow fiber membrane is from 8% inclusive to less than 25%.

16. The hollow fiber membrane module according to claim 1, wherein said hydrophilic polymer is crosslinked and insolubilized.

17. A process for manufacturing a hollow fiber membrane module, which method comprises
(i) providing a hollow fiber membrane module comprising polysulfone type selectively permeable hollow fiber membranes which contain a polysulfone-based resin and a hydrophilic polymer as main components, wherein
(A) the content of the hydrophilic polymer in the uppermost layer of the inner surface of said hollow fiber membrane is at least 1.1 times larger than the content of the hydrophilic polymer in the proximate layer of the inner surface of said membrane, and
(B) the content of the hydrophilic polymer in the uppermost layer of the outer surface of said hollow fiber membrane is at least 1.1 times larger than the content of the hydrophilic polymer in the uppermost layer of the inner surface of said membrane, and
(ii) exposing said hollow fiber membrane module to a radioactive ray, on condition that the oxygen concentration of an ambient atmosphere around said hollow fiber membrane is from 0.001 to 0.1%, and that the moisture content of said hollow fiber membrane to the weight thereof is from 0.2 to 7 mass %.

18. The process according to claim 17, wherein said radiation exposure is done while said hollow fiber membrane module is sealed in a packaging bag.

19. The process according to claim 17, wherein said radiation exposure is done under an internal atmosphere of said bag, of which the relative humidity is higher than 40% RH at 25° C.

20. The process according to claim 17, wherein said radiation exposure is done after at least 10 hours has passed since an oxygen scavenger was put in the packaging bag.

21. The process according to claim 17, wherein the amount of hydrogen peroxide eluted from the hollow fiber membrane which is removed from the hollow fiber membrane module after at least 3 months has passed since the radiation exposure is not larger than 10 ppm.

22. The process according to claim 17, wherein the uppermost layer of the inner surface of the polysulfone type hollow fiber membrane is a layer having a depth of up to 10 nm from the inner surface of the hollow fiber membrane, and the proximate layer is a layer having a depth of from 1,000 to 1,500 nm (from 1 to 1.5 μm) from the inner surface of the hollow fiber membrane.

23. The process according to claim 17, wherein the content of the hydrophilic polymer in the polysulfone type hollow fiber membrane is 20 to 40 mass % in the uppermost layer of the inner surface, 5 to 20 mass % in the proximate layer thereof, and 25 to 50 mass % in the uppermost layer of the outer surface.

24. The process according to claim 17, which said hollow fiber membrane module comprises 99 to 80 mass % of the polysulfone-based resin and 1 to 20 mass % of the hydrophilic polymer as main components.

25. The process according to claim 17, wherein the amount of the hydrophilic polymer eluted from the hollow fiber membrane is not larger than 10 ppm.

* * * * *